United States Patent [19]

Gutzwiller et al.

[11] 4,096,146

[45] Jun. 20, 1978

[54] 4-[5(R)-ALKYL(OR ALKENYL)-4(S)-QUINUCLIDIN-2(S) OR 2(R)-YLCARBONYL]-QUINOLINES, ANTIPODES OR RACEMATES THEREOF AND PROCESSES FOR THEIR PREPARATION

[75] Inventors: Juerg Albert Walter Gutzwiller, Bettingen, Switzerland; Milan Radoje Uskokovic, Upper Montclair, N.J.

[73] Assignee: Hoffmann-La Roche Inc., Nutley, N.J.

[21] Appl. No.: 606,252

[22] Filed: Aug. 20, 1975

Related U.S. Application Data

[60] Continuation of Ser. No. 354,839, Apr. 26, 1973, abandoned, which is a division of Ser. No. 212,648, Dec. 27, 1971, Pat. No. 3,753,992, which is a continuation-in-part of Ser. No. 104,785, Jan. 7, 1971, abandoned, which is a continuation-in-part of Ser. No. 837,304, Jun. 27, 1969, abandoned, which is a continuation-in-part of Ser. No. 741,913, Jul. 2, 1968, abandoned.

[51] Int. Cl.$^2$ ........................................... C07D 453/04
[52] U.S. Cl. ............................. 260/284; 260/288 CE; 424/258
[58] Field of Search ..................... 260/284, 288 CE

[56] References Cited

U.S. PATENT DOCUMENTS

| | | | |
|---|---|---|---|
| 2,226,568 | 12/1940 | Marks | 260/284 R |
| 2,492,487 | 12/1949 | Koepfli et al. | 260/288 R |
| 2,502,264 | 3/1950 | Lutz et al. | 260/288 R |
| 3,163,653 | 12/1964 | Ochaia et al. | 260/284 R |
| 3,238,212 | 3/1966 | Brossi et al. | 260/288 R |
| 3,663,552 | 5/1972 | Yardley et al. | 260/284 R |
| 3,907,806 | 9/1975 | Grethe et al. | 260/284 |
| 3,914,235 | 10/1975 | Gutzwiller et al. | 260/284 |
| 3,929,745 | 12/1975 | Gutzwiller et al. | 260/284 |
| 3,953,453 | 4/1976 | Grethe et al. | 260/284 |
| 4,012,396 | 3/1975 | Grethe et al. | 260/284 |

OTHER PUBLICATIONS

Renfrew et al.; Chemical Review; pp. 49–57 (1941).
Manske et al., The Alkaloids Chemistry and Physiology, vol. III, pp. 28–30 (1953).

*Primary Examiner*—Donald G. Daus
*Assistant Examiner*—Mary Vaughn
*Attorney, Agent, or Firm*—Samuel L. Welt; George M. Gould; William G. Isgro

[57] ABSTRACT

Quinine, quinidine, their antipodes or racemates and derivatives thereof, are prepared by (a) cyclizing the correspondingly substituted 4-[3-(1-chloro-3(R)-alkyl(or alkenyl)-4-(R)-piperidyl)-1-oxopropyl]quinolines, antipodes or racemates thereof, to the corresponding 4-[5(R)-alkyl(or alkenyl)-4-(S)-quinuclidin-2(S) or 2(R)-ylcarbonyl]quinolines, antipodes or racemates thereof; and (b) stereoselectively reducing the products of step (a) to α (S)-[5(R)-alkyl(or alkenyl)-4(S)-quinuclidin-2(R)-yl]-4-quinoline-methanols, antipodes or racemates thereof, and α(R)-[5(R)-alkyl(or alkenyl)-4(S)-quinuclidin-2(S)-yl]-4-quinolinemethanols, antipodes or racemates thereof. Various intermediates and the end products are useful antimalarial and antiarrhythmic agents.

4 Claims, No Drawings

4-[5(R)-ALKYL(OR ALKENYL)-4(S)-QUINUCLIDIN-2(S) OR 2(R)-YLCARBONYL]-QUINOLINES, ANTIPODES OR RACEMATES THEREOF AND PROCESSES FOR THEIR PREPARATION

CROSS-REFERENCE TO RELATED APPLICATIONS

This application is a continuation of U.S. Pat. application Ser. No. 354,839, filed Apr. 26, 1973, now abandoned, which in turn is a division of U.S. Pat. application Ser. No. 212,648, filed Dec. 27, 1971, now U.S. Pat. No. 3,753,992, issued Aug. 21, 1973, which in turn is a continuation-in-part of application Ser. No. 104,785, filed Jan. 7, 1971, now abandoned, which is a continuation-in-part of application Ser. No. 837,304, filed June 27, 1969, now abandoned, which is a continuation-in-part of application Ser. No. 741,913, filed July 2, 1968, now abandoned.

SUMMARY OF THE INVENTION

The invention relates to a process for preparing quinine, quinidine and derivatives thereof which is exemplified by the following reaction scheme:

In another aspect, the invention relates to compounds of the formulas

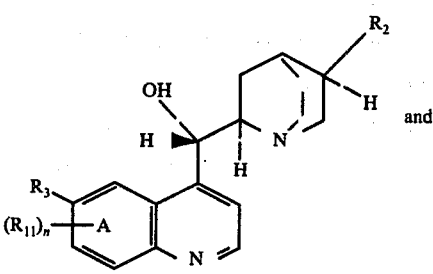

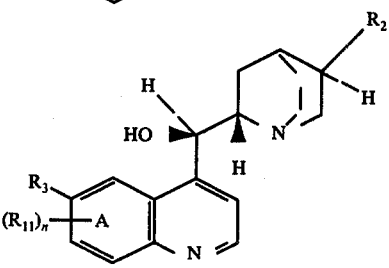

antipodes and racemates thereof;

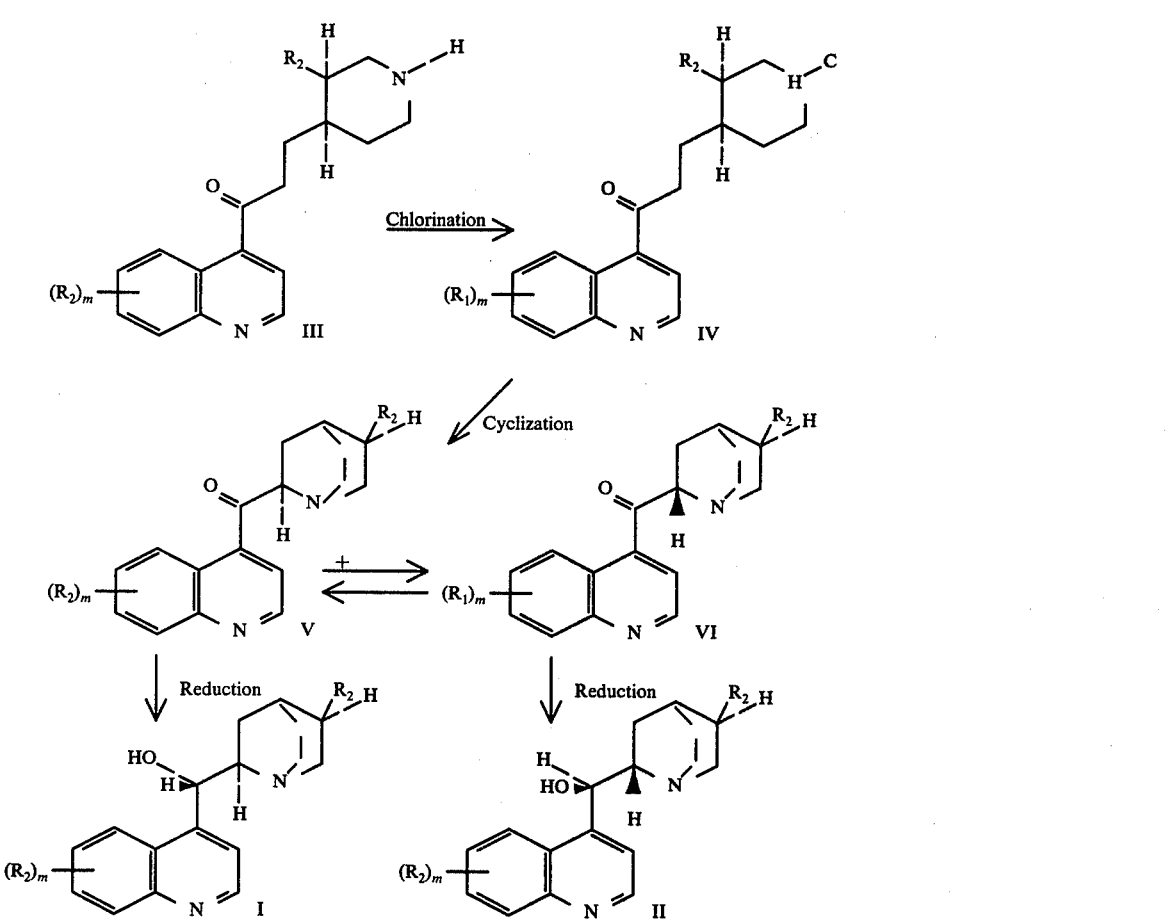

antipodes and racemates thereof;
wherein $m$ is 0, 1 or 2; $R_1$ is hydrogen, hydroxy, halogen, lower alkyl, lower alkoxy, trifluoromethyl, or, when $m$ is 2, $R_1$ taken together with an adjacent $R_1$ is also methylenedioxy; and $R_2$ is lower alkyl or lower alkenyl.

wherein $n$ is 1 or 2; $R_2$ is lower alkyl or lower alkenyl; $R_{11}$ is hydrogen, hydroxy, lower alkyl, lower alkoxy, trifluoromethyl, halogen, or, when $n$ is 2, $R_{11}$ taken together with an adjacent $R_{11}$ is also methylenedioxy; when $R_{11}$ is hydrogen, $R_3$ is lower alkyl, trifluoromethyl or halogen; when $R_{11}$ is other than hydrogen and $n$ is 1, $R_3$ is lower alkoxy, lower alkyl, hydrogen, trifluoromethyl, halogen, or taken together with an adjacent $R_{11}$ is methylenedioxy; and when $R_{11}$ is other than hydrogen and n is 2, $R_3$ is hydrogen, and pharmaceutically acceptable acid addition salts thereof.

The compounds of Formulas Ic and IIc are useful antimalarial and antiarrhythmic agents.

In a further aspect, the invention relates to compounds of the formulas

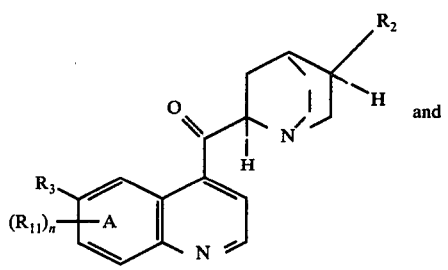

antipodes and racemates thereof;

wherein $R_2$, $R_3$, $R_{11}$ and n are as previously described, and pharmaceutically acceptable acid addition salts thereof.

The compounds of Formulas Vc and VIc are useful as intermediates and as antimalarial and antiarrhythmic agents.

In still a further aspect, the invention relates to compounds of the formulas antipodes and racemates thereof antipodes and racemates thereof and antipodes and racemates thereof;

wherein $R_1$, $R_2$, $R_3$, $R_{11}$, m and n are as previously described, and $R_3$ is lower alkyl.

The compounds of Formulas IXa, IIIc and IV are useful as intermediates in the process of the invention.

DETAILED DESCRIPTION OF THE INVENTION

The term "lower alkyl" as used herein denotes a hydrocarbon group containing 1–7 carbon atoms, such as methyl, ethyl, propyl, butyl and the like; ethyl is preferred. The term "lower alkoxy" denotes a lower alkyl ether group in which the lower alkyl moiety is described as above. The term "lower alkenyl" as used herein denotes a hydrocarbon group containing 2–7 carbon atoms, such as vinyl, propenyl, butenyl and the like. Preferred is vinyl. The term "halogen" denotes all of the halogens, i.e., bromine, chlorine, fluorine and iodine.

As is evident from the above $R_1$ or $R_{11}$ or the like are individually selected from the various groupings hereinbefore described. Moreover, when m or n is 2, $R_1$ or $R_{11}$ or the like can additionally form with an adjacent $R_1$ or $R_{11}$ or the like the methylenedioxy radical. Thus, either when m or n is 1 or 2, $R_1$ or $R_{11}$ or the like can individually also represent hydrogen, hydroxy, halogen, lower alkyl, lower alkoxy or trifluoromethyl. Additionally, when m or n is 2, two adjacent groupings of $R_1$ or $R_{11}$ can together represent methylenedioxy.

The process aspect of the invention is exemplified by Reaction Scheme I:

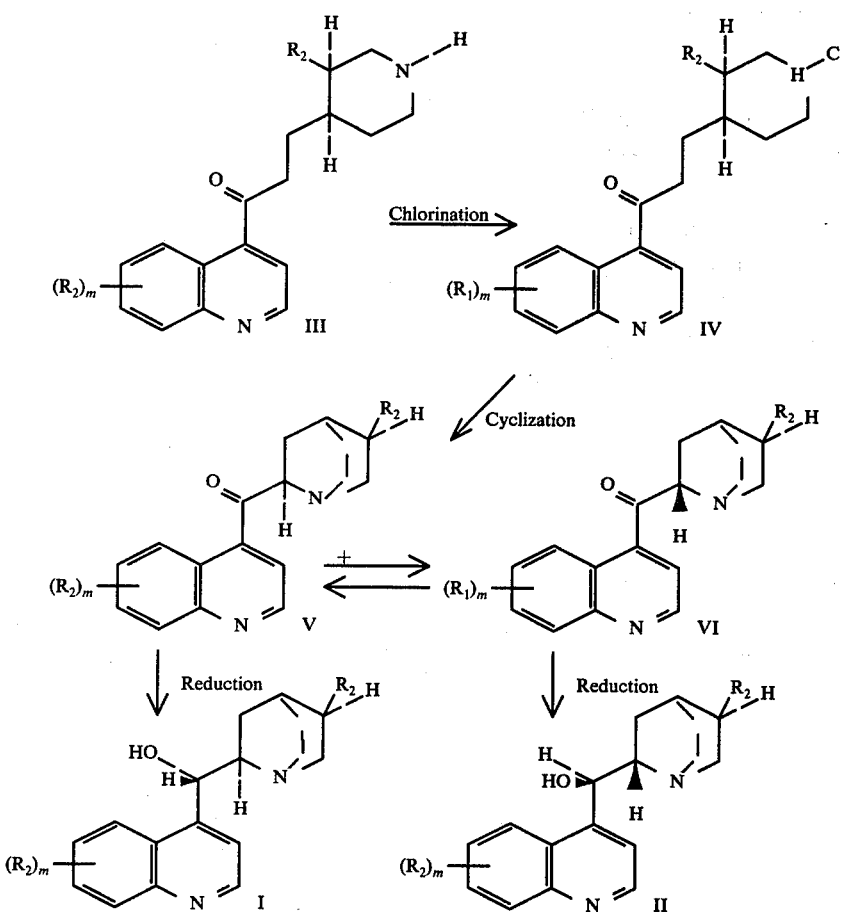

antipodes and racemates thereof wherein $m$ is 0, 1 or 2; $R_1$ is hydrogen, hydroxy, halogen, lower alkyl, lower alkoxy or trifluoromethyl, or, when $m$ is 2, $R_1$ taken together with an adjacent $R_1$ is also methylenedioxy; and $R_2$ is lower alkyl or lower alkenyl.

In Reaction Scheme I, the 4-[3-(3(R)-alkyl(or alkenyl)-piperid-4(R)-yl)-1-oxopropyl]quinolines of Formula III, antipodes or racemates thereof, are converted to the corresponding 4-[3-(1-chloro-3(R)-alkyl(or alkenyl)-piperid-4(R)-yl)-1-oxopropyl] quinolines of Formula IV, antipodes or racemates thereof, utilizing a chlorinating agent such as sodium hypochlorite, N-chlorosuccinimide or the like. The chlorination is suitably carried out at room temperature or above, preferably at a temperature between 20° and 50° C. Moreover, the chlorination can be suitably carried out in the presence of an inert organic solvent, for example, a hydrocarbon such as benzene, a halogenated hydrocarbon such as dichloromethane or chloroform, or an ether such as ether or dioxane.

The 4-[3-(1-chloro-3(R)-alkyl(or alkenyl)piperid-4(R)-yl)-1-oxopropyl]quinolines of Formula IV, antipodes or racemates thereof, are converted to the corresponding epimeric 4-[5(R)-alkyl(or alkenyl)-4(S)-quinuclidin-2(R)-ylcarbonyl]quinolines of Formula V, antipodes or racemates thereof, and 4-[5(R)-alkyl(or alkenyl)-4(S)-quniuclidin-2(S)-ylcarbonyl]quinolines of Formula VI, antipodes or racemates thereof, under acidic conditions, utilizing a cyclizing agent. Exemplary of such agents are inorganic or organic acids such as mineral acids, for example, phosphoric acid and sulfuric acid; strong alkanoic acids, for example, trichloroacetic acid; and mixtures thereof, for example, acetic/sulfuric acid. The reaction is conveniently carried out at room temperature or above, preferably at a temperature between 20° and 50° C. Moreover, the cyclization can be suitably carried out in the presence of an inert solvent of the type previously described. As mentioned above, the cyclization yields a mixture of the epimeric compounds of Formulas V and VI, which can be reacted further as such or can be separated into the respective epimers utilizing methods such as crystallization, and the like, and such epimer reacted separately.

The conversion of the 4-[5(R)-alkyl(or alkenyl)-4(S)-quinuclidin-2(R)-ylcarbonyl]quinolines of Formula V, antipodes or racemates thereof to α(S)-[5(R)-alkyl(or alkenyl)-4(S)-quinuclidin-2(R)-yl]-4-quinolinemethanols of Formula I, antipodes or racemates thereof, respectively, is carried out utilizing a stereoselective reducing agent, for example, a dialkylaluminum hydride, such as diisobutylaluminum hydride or the like. The reduction is suitably carried out at room temperature; however, temperatures above or below room temperature may be employed. It is preferred to employ a temperature between 20° C. and 50° C. The reduction can be conveniently conducted in the presence of an inert organic solvent, for example, a hydrocarbon such as benzene or toluene, or an ether such as diethylether, tetrahydrofuran or the like.

The conversion of the compounds of Formula V or their racemates to those of Formula I, antipodes or racemates thereof, respectively, when $R_2$ is lower alkyl, can also be effected utilizing a hydrogenation catalyst such as nickel, palladium, ruthenium, copper or barium chromite in the presence of a solvent, for example, an aqueous or non-aqueous alkanol such as methanol or ethanol, or an ether such as dioxane. When $R_2$ is lower alkyl or lower alkenyl, the conversion can be effected utilizing a hydrogenation agent such as aluminum in methanol, sodium isopropoxide in toluene, lithium aluminum hydride, aluminum hydride, chloroaluminum hydride, dichloroaluminum hydride, bromoaluminum hydride, dibromoaluminum hydride, lithium tri-tert.-butoxyaluminum hydride in ether, tetrahydrofuran, dioxane or the like.

The conversion of the 4-[5(R)-alkyl(or alkenyl)-4(S)-quinuclidin-2(S)-ylcarbonyl]quinolines of Formula VI, antipodes or racemates thereof, to the α(R)-alkyl(or alkenyl)-4(S)-quinuclidin-2(S)-yl]-4-quinolinemethanols of Formula II, antipodes or racemates thereof, respectively, is carried out according to the procedures described for the conversion of the compounds of Formula V.

The 4-{3-[3(R)-alkyl(or alkenyl)-piperid-4(R)-yl]-1-oxopropyl}-quinolines of Formula III, antipodes or racemates thereof, can be cyclized to the 4-[5(R)-alkyl(or alkenyl)-4(S)-quinuclidin-2(R) (or 2(S))-ylcarbonyl]quinolines of Formula V–VI, antipodes or racemates thereof, respectively, according to the reaction set forth in Scheme III:

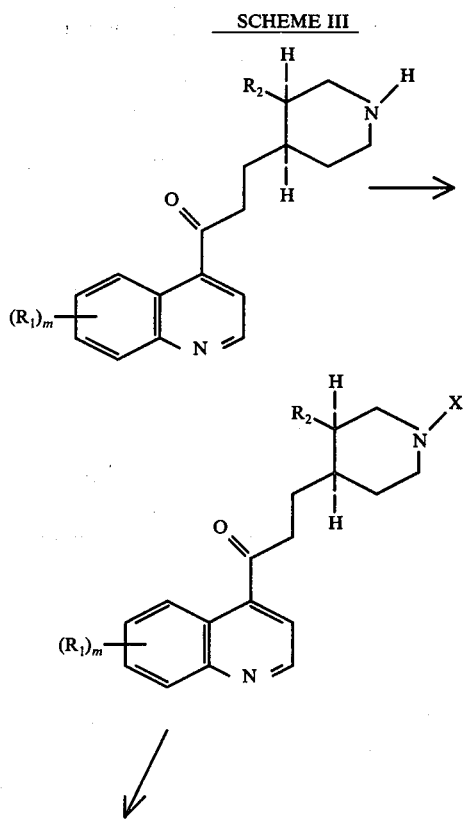

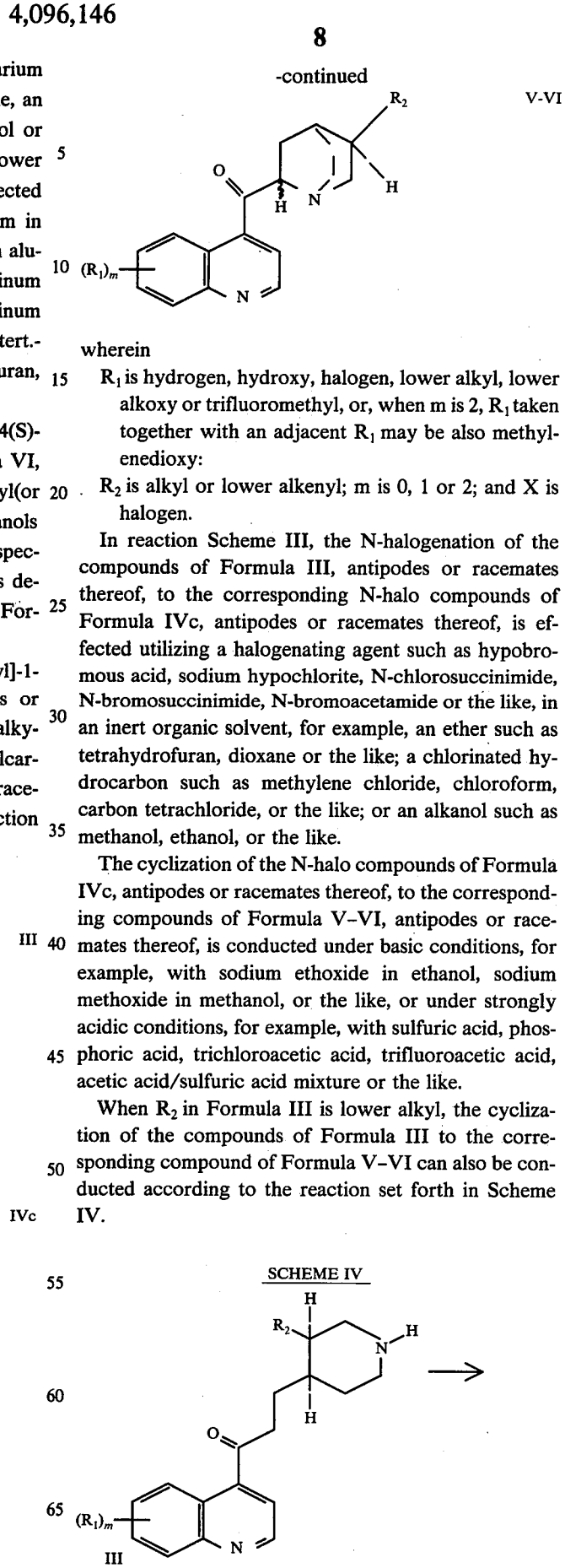

wherein
$R_1$ is hydrogen, hydroxy, halogen, lower alkyl, lower alkoxy or trifluoromethyl, or, when m is 2, $R_1$ taken together with an adjacent $R_1$ may be also methylenedioxy;
$R_2$ is alkyl or lower alkenyl; m is 0, 1 or 2; and X is halogen.

In reaction Scheme III, the N-halogenation of the compounds of Formula III, antipodes or racemates thereof, to the corresponding N-halo compounds of Formula IVc, antipodes or racemates thereof, is effected utilizing a halogenating agent such as hypobromous acid, sodium hypochlorite, N-chlorosuccinimide, N-bromosuccinimide, N-bromoacetamide or the like, in an inert organic solvent, for example, an ether such as tetrahydrofuran, dioxane or the like; a chlorinated hydrocarbon such as methylene chloride, chloroform, carbon tetrachloride, or the like; or an alkanol such as methanol, ethanol, or the like.

The cyclization of the N-halo compounds of Formula IVc, antipodes or racemates thereof, to the corresponding compounds of Formula V–VI, antipodes or racemates thereof, is conducted under basic conditions, for example, with sodium ethoxide in ethanol, sodium methoxide in methanol, or the like, or under strongly acidic conditions, for example, with sulfuric acid, phosphoric acid, trichloroacetic acid, trifluoroacetic acid, acetic acid/sulfuric acid mixture or the like.

When $R_2$ in Formula III is lower alkyl, the cyclization of the compounds of Formula III to the corresponding compound of Formula V–VI can also be conducted according to the reaction set forth in Scheme IV.

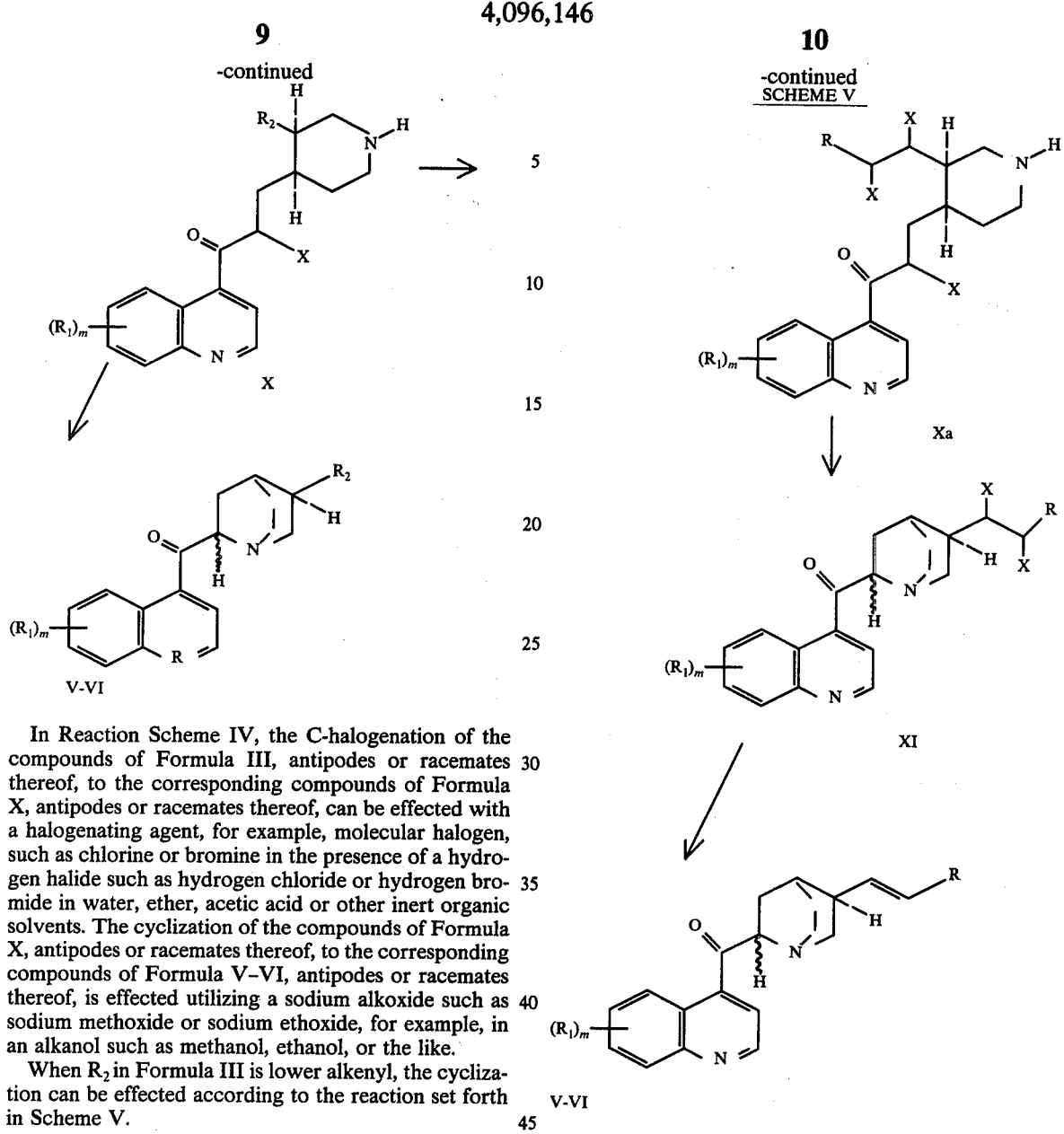

In Reaction Scheme IV, the C-halogenation of the compounds of Formula III, antipodes or racemates thereof, to the corresponding compounds of Formula X, antipodes or racemates thereof, can be effected with a halogenating agent, for example, molecular halogen, such as chlorine or bromine in the presence of a hydrogen halide such as hydrogen chloride or hydrogen bromide in water, ether, acetic acid or other inert organic solvents. The cyclization of the compounds of Formula X, antipodes or racemates thereof, to the corresponding compounds of Formula V–VI, antipodes or racemates thereof, is effected utilizing a sodium alkoxide such as sodium methoxide or sodium ethoxide, for example, in an alkanol such as methanol, ethanol, or the like.

When $R_2$ in Formula III is lower alkenyl, the cyclization can be effected according to the reaction set forth in Scheme V.

SCHEME V

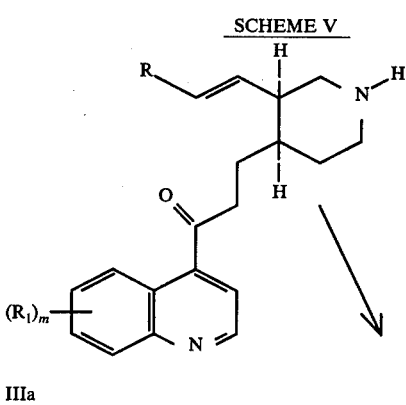

wherein R is lower alkyl.

In Reaction Scheme V, the halogenation of the compounds of Formula IIIa, antipodes or racemates thereof, to the corresponding compounds of Formula Xa, antipodes or racemates thereof, is effected utilizing a halogenating agent, for example, molecular halogen, such as chlorine or bromine in the presence of a halogen halide, such as hydrogen chloride or hydrogen bromide in water, ether, acetic acid or other inert organic solvents. The cyclization of the compounds of Formula Xa, antipodes or racemates thereof, to the corresponding compounds of Formula XI, antipodes or racemates thereof, is effected utilizing a sodium alkoxide such as sodium methoxide or sodium ethoxide in an alkanol such as methanol, ethanol or the like. The dehalogenation of the compounds of Formula XI, antipodes or racemates thereof, to the corresponding compounds of Formula V–VI, antipodes or racemates thereof, is effected with, for example, sodium iodide.

Scheme 1(a)

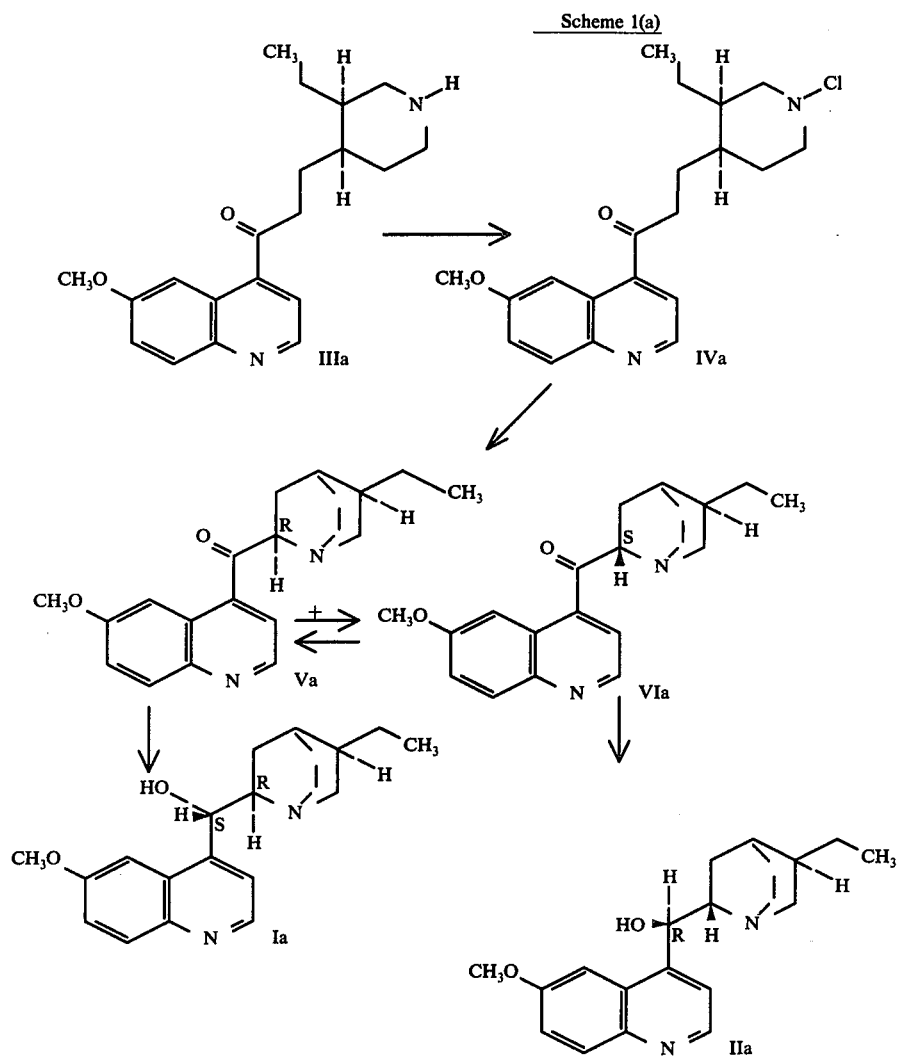

antipodes or racemates thereof.

Reaction Scheme Ia represents a preferred embodiment of Reaction Scheme I, i.e., the preparation of dihydroquinidine and dihydroquinine, and is carried out utilizing the reaction conditions set forth for Reaction Scheme I. In Reaction Scheme Ia, dihydroquinotoxine of Formula IIIa, antipode or racemate thereof, is converted to N-chloro-dihydroquinotoxine of Formula IVa, antipode or racemate thereof. The N-chloro-dihydroquinotoxine of Formula IVa, antipode or racemate thereof, is converted to the epimeric dihydroquinidinone of Formula Va, antipode or racemate thereof, and dihydroquininone of Formula VIa, antipode or racemate thereof, which are in turn converted to dihydroquinidine or Formula Ia, antipode or racemate thereof, and dihydroquinine of Formula IIa, antipode or racemate thereof, respectively.

Scheme 1(b)

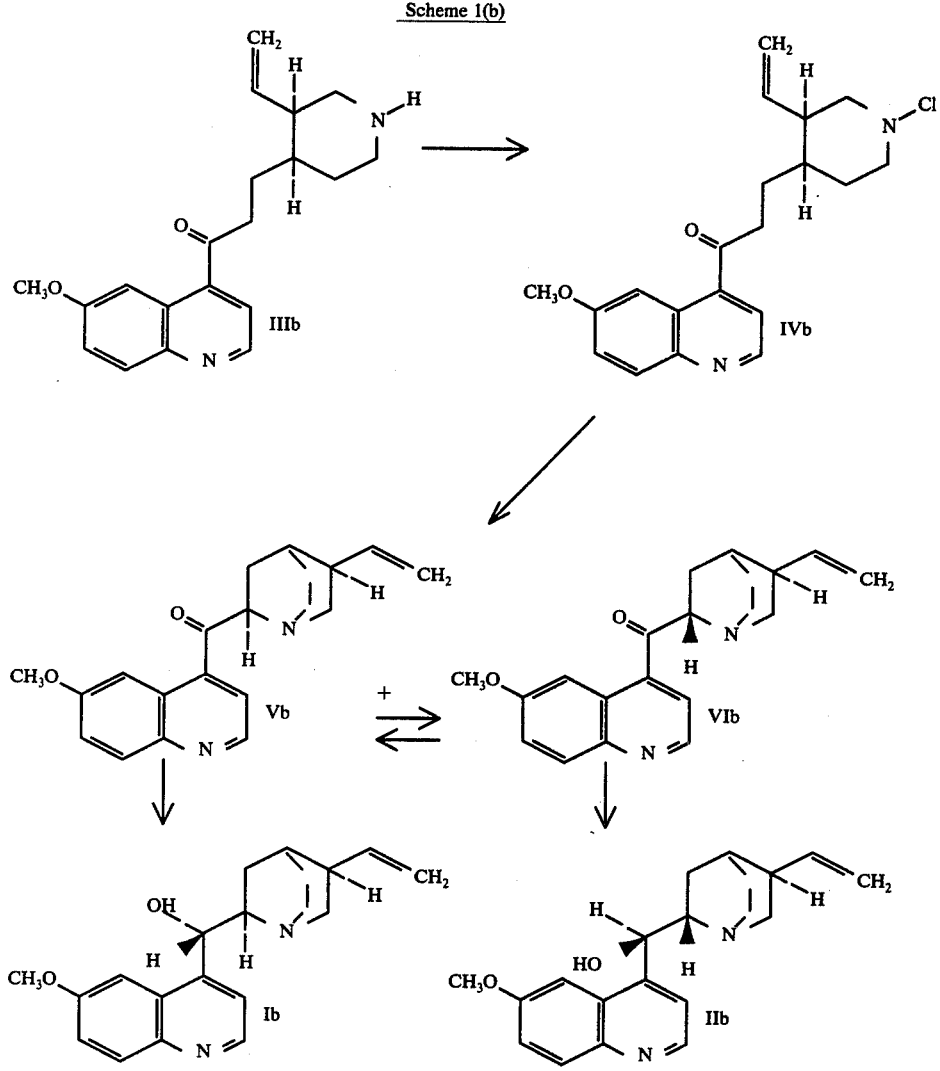

Reaction Scheme Ib represents another preferred embodiment of Reaction Scheme I, i.e., the preparation of quinidine and quinine, antipodes or racemates thereof, and is carried out utilizing the reaction conditions set forth in Reaction Scheme I. In Reaction Scheme Ib, quinotoxine of Formula IIIb, antipode or racemate thereof, is converted to N-chloro-quinotoxine of Formula IVb, antipode or racemate thereof. The N-chloroquinotoxine of Formula IVb, antipode or racemate thereof, is converted to quinidinone of Formula Vb, antipode or racemate thereof, and quininone of Formula VIb, antipode or racemate thereof, which in turn converted to quinidine of Formula Ib, antipode or racemate thereof, and quinine of Formula IIb, antipode or racemate thereof, respectively.

SCHEME II

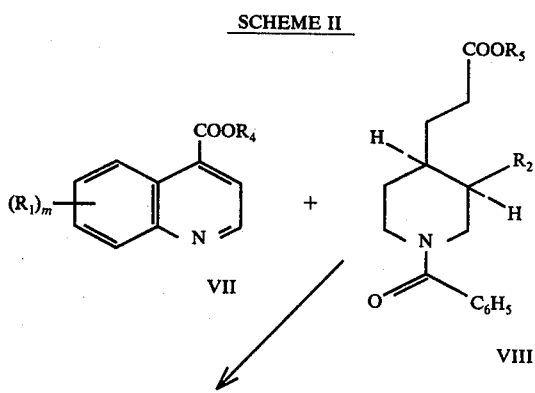

SCHEME II -continued

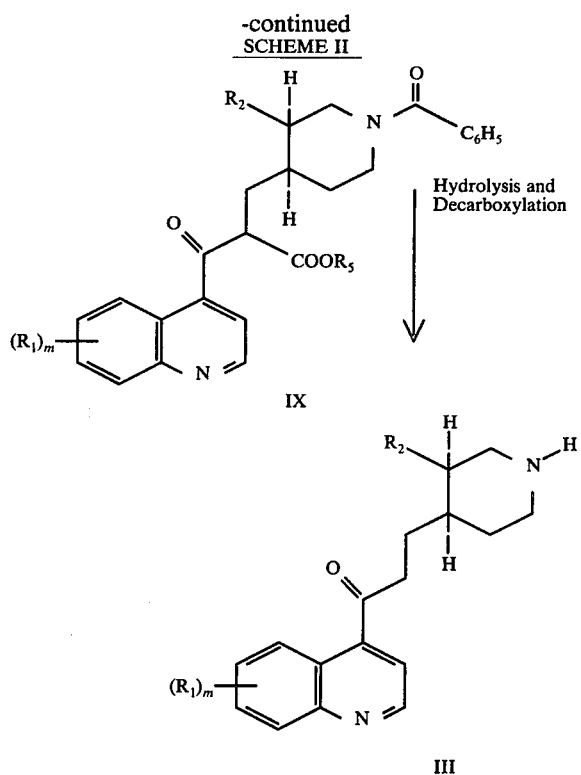

SCHEME III

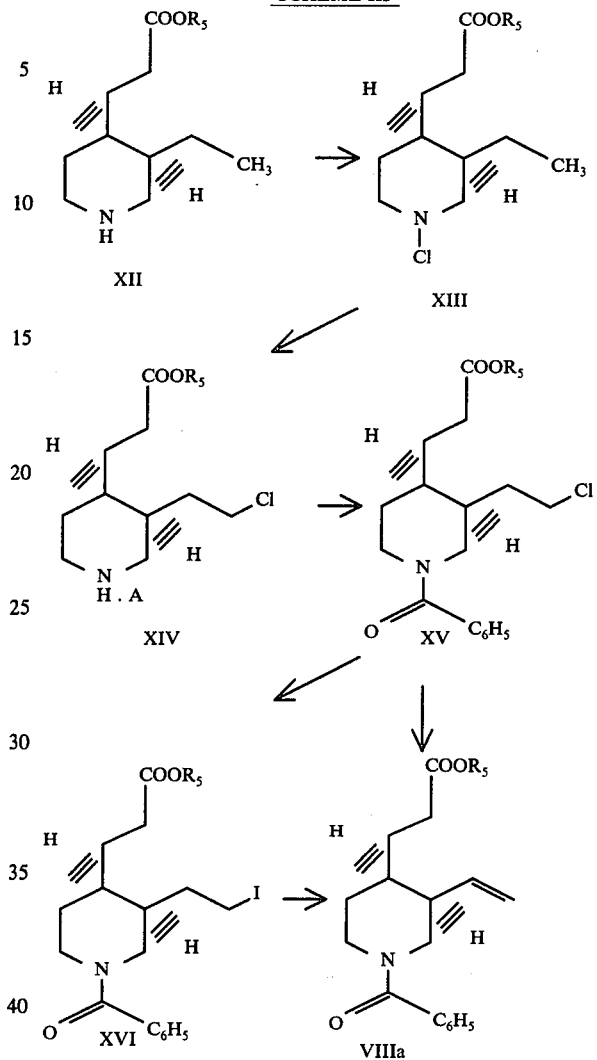

antipodes or racemates thereof
wherein $R_1$, $R_2$ and m are as previously described; and $R_4$ and $R_5$ are lower alkyl.

In Reaction Scheme II, the cinchoninic acid lower alkyl esters of Formula VII, which are known or are analogs of known compounds readily obtained by known procedures, are reacted in the presence of a base, for example, alkaline metal alkoxides, such as sodium methoxide, sodium ethoxide, potassium tertiary butoxide and the like, with the 1-benzoyl-3(R)-alkyl(or alkenyl)-4(R)-piperidinepropionic acid esters of Formula VIII, antipodes or racemates thereof, which are known compounds or are analogs of known compounds readily obtained by known procedures, or by the procedure hereinafter described in Scheme III, to yield the corresponding α-[1-benzoyl-3(R)-alkyl(or alkenyl)-4(R)-piperidyl-methyl]-β-oxo-4-quinolinepropionic acid esters of Formula IX, antipodes or racemates thereof. The reaction is conveniently conducted at reflux temperatures; however, lower temperatures may also be employed. An inert solvent, for example, ethers such as tetrahydrofuran, dioxane and the like, may also be conveniently employed.

The conversion of the α-[1-benzoyl-3(R)-alkyl(or alkenyl)-4(R)-piperidyl-methyl]-β-oxo-4-quinolinepropionic acid esters of Formula IX to the corresponding 5-[3-(3(R)-alkyl(or alkenyl)-4(R)-piperidyl)-1-oxopropyl]quinolines of Formula III is effected utilizing a hydrolyzing agent such as hydrochloric acid at reflux temperatures. Conveniently, temperatures below reflux may also be utilized.

The preparation of the 1-benzoyl-3(R)-alkenyl-4(R)-piperidine-propionic acid esters of Formula VIII, antipodes or racemates thereof, can be carried out as set forth in Reaction Scheme III.

wherein $R_5$ is as previously described, and A is an inorganic acid such as sulfuric acid, phosphoric acid and the like, or organic acids, for example, lower alkanoic acids such as acetic acid, and the like, halogenated lower alkanoic acids such as trifluoroacetic acid, trichloroacetic acid and the like.

In Reaction Scheme III, the 3(R)-ethyl-4(R)-piperidinepropionic acid esters of Formula XII, antipodes or racemates thereof, which are known compounds, are converted to the corresponding 1-chloro-3(R)-ethyl-4(R)-piperidine propionic acid esters of Formula XIII, antipodes or racemates thereof, by utilizng a chlorinating agent, for example, N-chlorosuccinimide, N-chloroacetamide, alkali metal hypochlorite such as sodium hypochlorite and the like. The reaction is conducted in an inert organic solvent, for example, a hydrocarbon such as benzene, a halogenated hydrocarbon such as dichloromethane, an alkanol such as methanol, ethanol and the like, an ether such as diethylether, dioxane, tetrahydrofuran and the like. The reaction temperature is not critical; however, preferably, it is in the range of about 0° C. and about room temperature.

The conversion of the compounds of Formula XIII, their antipodes or racemates, to the corresponding 3(R)-(2-chloroethyl)-4-(R)-piperidinepropionic acid ester salts of the Formula XIV, antipodes or racemates thereof, is effected by irradiation with ultraviolet light source such as a 200W-Hannovia high pressure mercury lamp in an acid such as previously described. The reaction temperature is not critical; however, preferably it is in the range of about 0° C. to about room temperature.

The conversion of the compounds of Formula XIV, antipodes or racemates thereof, to corresponding 1-benzoyl-3(R)-(2-chloroethyl)-4-(R)-piperidinepropionic acid esters of Formula XV, antipodes or racemates thereof, is effected utilizing a benzoyl halide such as benzoyl chloride, in an inert organic solvent, for example, a hydrocarbon such as benzene, toluene and the like, a halogenated such as dichloromethane, chloroform and the like, or ethers such as diethyl ethers, tetrahydrofuran, dioxane and the like. The pH of the reaction mixture is maintained between about 6 to about 9 utilizing, for example, alkali metal carbonates such as sodium or potassium carbonate. The reaction temperature is not critical; however, preferably it is in the range of about 0° C. and about room temperature.

The conversion of the compounds of Formula XV, antipodes or racemates thereof, to the corresponding 1-benzoyl-3(R)-(2- iodoethyl)-4(R)-piperidinepropionic acid esters of the Formula XVI, antipodes or racemates thereof, is effected utilizing an alkali metal iodide such as potassium iodide, sodium iodide and the like, in an inert organic solvent, for example, dimethylsulfoxide, dimethylformamide, acetonitrile, alkanols such as methanol, ethanol and the like, or ketones such as acetone, methylethylketone and the like. The temperature is not critical; however, preferably it is in the range of about 0° C. and about the reflux of the reaction mixture.

The conversion of the compounds of Formula XVI, antipodes or racemates thereof, to the corresponding 1-benzoyl-3(R)-vinyl-4(R)-piperidinepropionic acid esters of the Formula VIIIa, antipodes or racemates thereof, is effected utilizing an organic base, for example, pyridine, β-collidine, dimethylformamide and the like. Advantageously, an inorganic salt, for example, lithium bromide, lithium chloride, lithium carbonate, silver fluoride, silver carbonate and the like, may be utilized in the reaction. The reaction temperature is not critical; however, preferably it is in the range of about room temperature and about the reflux temperature of the reaction mixture.

The conversion of the compounds of Formula XV, antipodes or racemates thereof, to the corresponding 1-benzoyl-3(R)-vinyl-4(R)-piperidinepropionic acid esters of the Formula VIIIa, antipodes or racemates thereof, is effected by pyrrolysis, preferably at a temperature in the range of 150° C. and about 250° C. The reaction can be conducted at atmospheric pressure; however, preferably is conducted at reduced pressure, for example, in the range of about .1 mm/Hg to .01 mm/Hg.

In still another aspect, the invention comprises the process illustrated by Reaction Scheme VI:

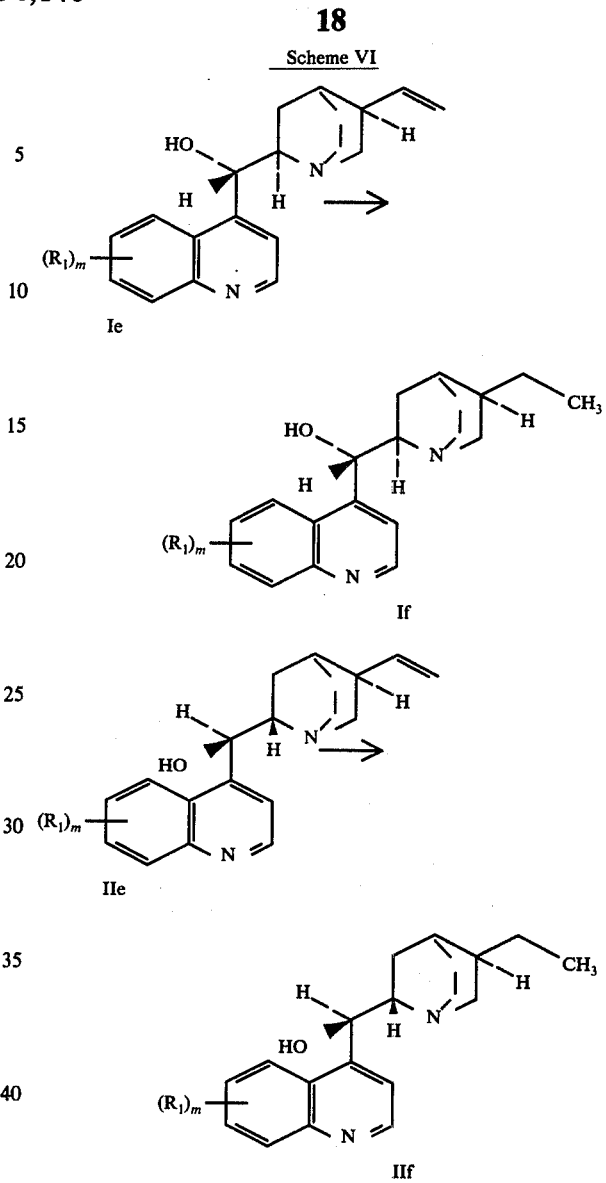

Scheme VI wherein $R_1$ and $m$ are as previously described.

In Reaction Scheme VI the conversion of the α(S)-[5(R)-vinyl-4(S)-quinuclidin-2(R)-yl]-4-quinolinemethanols of formula Ie or of the α(R)-[5(R)-vinyl-4(S)-quinuclidin-2(S)-yl]-4-quinolinemethanols of formula IIe to the α(S)-[5(R)-ethyl-4(S)-quinuclidin-2(R)-yl]-4-quinolinemethanols of formula If or to the α(R)-[5(R)-ethyl-4(S)-quinuclidin-2(S)-yl]-4-quinolinemethanols of formula IIf, respectively, is effected by catalytic hydrogenation utilizing, for example, a noble metal, such as palladium, platinum or the like. Conveniently, the hydrogenation is carried out in an inert solvent, for example, in water, an alkanol, such as methanol, ethanol or the like, or an organic or inorganic acid, such as acetic acid, hydrochloric acid or the like, or mixtures thereof. Further, the hydrogenation is suitably carried out at room temperature; however, temperatures above or below room temperature may be employed. Alternatively, the conversion can be effected by a chemical reduction in the presence of oxygen, utilizing hydrazine hydrate and a cupric salt, such as cupric sulfate, as the catalytic agent. Conveniently, the reduction is carried out in a polar solvent, for example, water or a lower alkanol, such as methanol or ethanol, preferably at a temperature in the range of room temperature and the boiling temperature of the reaction mixture.

In another aspect, the invention relates to compounds of the formulas

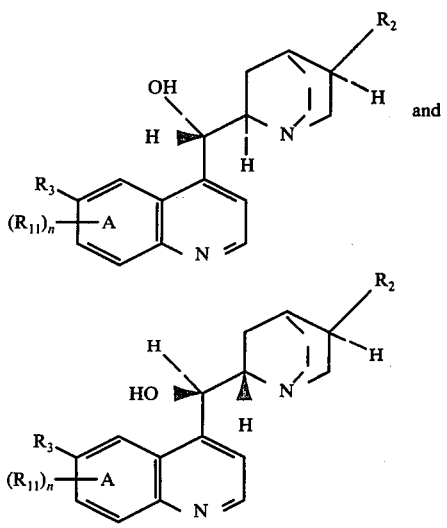

wherein n is 1 or 2; R₂ is lower alkyl or lower alkenyl;
R₁₁ is hydrogen, hydroxy, lower alkyl, lower alkoxy, trifluoromethyl or halogen, or, when n is 2, R₁₁ taken together with an adjacent R₁₁ is also methylenedioxy; when
R₁₁ is hydrogen, R₃ is lower alkyl, trifluoromethyl or halogen; when R₁₁ is other than hydrogen and n is 1, R₃ is lower alkoxy, lower alkyl, hydrogen, trifluoromethyl or halogen, or taken together with an adjacent R₁₁ is also methylenedioxy; and when R₁₁ is other than hydrogen and n is 2, R₃ is hydrogen,
and pharmaceutically acceptable acid addition salts thereof.

Exemplary of the compounds of Formulas Ic IIc are:
7-Methoxy-α(S)-[5(R)-ethyl-4(S)-quinuculidin-2(R)-yl]-4-quinolinemethanol [hereinafter referred to as 7'-methoxy-dihydrocinchonine], its antipode and racemic analog;
7-Methoxy-α(R)-[5(R)-ethyl-4(S)-quinuclidin-2(S)-yl]-4-quinolinemethanol] [hereinafter referred to as 7'-methoxy-dihydrocinchonidine], its antipode and racemic analog;
6,7-Dimethoxy-α(S)-[5(R)-ethyl-4(S)-quinuclidin-2(R)-yl]-4-quinolinemethanol [hereinafter referred to as 6',7'-dimethoxy-dihydrocinchonine], its antipode and racemic analog;
6,8-Dimethoxy-α(S)-[5(R)-ethyl-4(S)-quinuclidin-2(R)-yl]-4-quinolinemethanol, its antipode and racemic analog;
6,7-Dimethoxy-α(R)--[5(R)-ethyl-4(S)-quinuclidin-2(S)-yl]-4-quinolinemethanol [hereinafter referred to as 6',7'-dimethoxy-dihydrocinchonidine], its antipode and racemic analog;
6,8-Dimethoxy-α(R)-[5(R)-ethyl-4(S)-quinuclidin-2(S)-yl]-4-quinolinemethanol, its antipode and racemic analog;
6-Methoxy-α(S)-[5(R)-propyl-4(S)-quinuclidin-2(R)-yl]-4-quinolinemethanol, antipode and racemic analog;
6-Methoxy-α(R)-[5(R)-allyl-4(S)-quinuclidin-2(S)-yl]-4-quinolinemethanol, antipode and racemic analog;
6Methyl-α(S)-[5(R)-ethyl-4(S)-quinuclidin-2(R)-yl]-4-quinolinemethanol [hereinafter referred to as 6'-methyldihydrocinchonine], its antipode and racemic analog;
6Methyl-α(R)-[5(R)-ethyl-4(S)-quinuclidin-2(S)-yl]-4-quinolinemethanol [hereinafter referred to as 6'-methyldihydrocinchonidine], its antipode and racemic analog;
6-Chloro-α(S)-[5(R)-ethyl-4(S)-quinuclidin-2(R)-yl]-4-quinolinemethanol [hereinafter referred to as 6'-chloro-dihydrocinehonine], its antipode and racemic analog;
6-Chloro-α(R)-[5(R)-ethyl-4(S)-quinuclidin-2(S)-yl]-4-quinolinemethanol [hereinafter referred to as 6'-chloro-dihydrocinchonidine], its antipode and racemic analog;
7-Chloro-α(S)-[5(R)-ethyl-4(S)-quinuclindin-2(R)-yl]-4-quinolinemthanol [hereinafter referred to as 7'-chloro-dihydrocinchonine], its antipode and racemic analog;
7-Chloro-α(R)-[5(R)-ethyl-4(S)-quinuclidin-2(S)-yl]-4-quinclinemethanol [hereinafter referred to as 7'-chloro-dihydrocinchonidine], its antipode and racemic analog;
7-Chloro-α(S)-[5(R)-vinyl-4(S)-quinuclidin-2(R)-yl]-4-quinolinemthanol [hereinafter referred to as 7'-chloro-cinchonine], its antipode and racemic analog;
7-Chloro-α(R)-[5(R)-vinyl-4(S)-quinuclidin-2(S)-yl]-4-quinolinemethanol [hereinafter referred to as 7'-chloro-cinchonidine], its antipode and racemic analog;
6,7-Methylenedioxy-α(S)-[5(R)-vinyl-4(S)-quinuclidin-2(R)-yl]-4-quinolinemethanol [hereinafter referred to as 6',7'-methylenedioxy-cinchonine], its anitpode and racemic analog;
6,7-Methylenedioxy-α(R)-[5(R)-vinyl-4(S)-quinuclidin-2(S)-yl]-4-quinolinemthanol [hereinafter referred to as 6',7'-methylenedioxy-cinchonidine], its antipode and racemic analog;
6-Chloro-α(S)-[5(R)-vinyl-4(S)-quinuclidin-2(R)-yl]-4-quinolinemethanol [hereinafter referred to as 6'-chloro-cinchonine], its antipode and racemic analog;
6-Chloro-α(R)-[5(R)-vinyl-4(S)-quinuclidin-2(S)-yl]-4-quinolinemethanol [hereinafter referred to as 6'-chloro-cinchonidine], its antipode and racemic analog;
6,8-Dichloro-α(S)-[5(R)-vinyl-4(S)-quinuclidin-2(R)-yl]-4-quinolinemethanol [hereinafter referred to as 6',8'-dichloro-cinchonine], its antipode and racemic analog;
6,8-Dichloro-α(R)-[5(R)-vinyl-4(S)-quinuclidin-2(S)-yl]-4-quinolinemethanol [hereinafter referred to as 6', 8-dichloro-cinchonidine], its anitpode and racemic analog;
6,7-Methylenedioxy-α(S)-[5(R)-ethyl-4(S)-quinuclidin-2(R)-yl]-4-quinolinemethanol [hereinafter referred to as 6',7'-methylenedioxy-dihydrocinchonine], its antipode and racemic analog;
6,7-Methylenedioxy-α(R)-[5(R)-ethyl-4(S)-quinuclidin-2(S)-yl]-4-quinolinemethanol [hereinafter referred to as 6',7'-methylenedioxy-dihydrocinchonidine], its antipode and racemic analog;

7-Trifluoromethyl-α(S)-[5(R)-ethyl-4(S)-quinuclidin-2(R)-yl]-4-quinolinemethanol [hereinafter referred to as 7'-trifluoromethyldihydrocinchonine], its antipode and racemic analog;

7-Trifluoromethyl-α(R)-[5(R)-ethyl-4(S)-quinuclidin-2(S)-yl]-4-quinolinemethanol [hereinafter referred to as 7'-trifluoromethyldihydrocinchonidine], its antipode and racemic analog;

6,8-Dichloro-α(S)-[5(R)-ethyl-4(S)-quinuclidin-2(R)-yl]-4-quinolinemethanol [hereinafter referred to as 6',8'-dichlorodihydrocinchonine], its antipode and racemic analog;

6,8-Dichloro-α(R)-[5(R)-ethyl-4(S)-quinuclidin-2(S)-yl]-4-quinolinemethanol [hereinafter referred to as 6',8'-dichlorodihydrocinchonidine], its antipode and racemic analog.

7-Trifluoromethyl-α(S)-[5(R)-vinyl-4(S)-quinuclidin-2(R)-yl]-4-quinolinemethanol [hereinafter referred to as 7'-trifluoromethylcinchonine], its antipode and racemic analog;

7-Trifluoromethyl-α(R)-[5(R)-vinyl-4(S)-quinuclidin-2(S)-yl]-4-quinolinemethanol [hereinafter referred to as 7'-trifluoromethylcinchonidine], its antipode and racemic analog;

5-Trifluoromethyl-α(S)-[5(R)-vinyl-4(S)-quinuclidin-2(R)-yl]-4-quinolinemethanol [hereinafter referred to as 5'-trifluoromethylcinchonine], its antipode and racemic analog;

5-Trifluoromethyl-α(R)-[5(R)-vinyl-4(S)-quinuclidin-2(S)-yl]-4-quinolinemethanol [hereinafter referred to as 5'-trifluoromethylcinchonidine], its antipode and racemic analog;

6-Trifluoromethyl-α(S)-[5(R)-vinyl-4(S)-quinuclidin-2(R)-yl]-4-quinolinemethanol [hereinafter referred to as 6'-trifluoromethylcinchonine], its antipode and racemic analog;

6-Trifluoromethyl-α(R)-[5(R)-vinyl-4(S)-quinuclidin-2(S)-yl]-4-quinolinemethanol [hereinafter referred to as 6'-trifluoromethylcinchonidine], its anitpode and racemic analog.

In a further aspect, the invention relates to compounds of the formulas

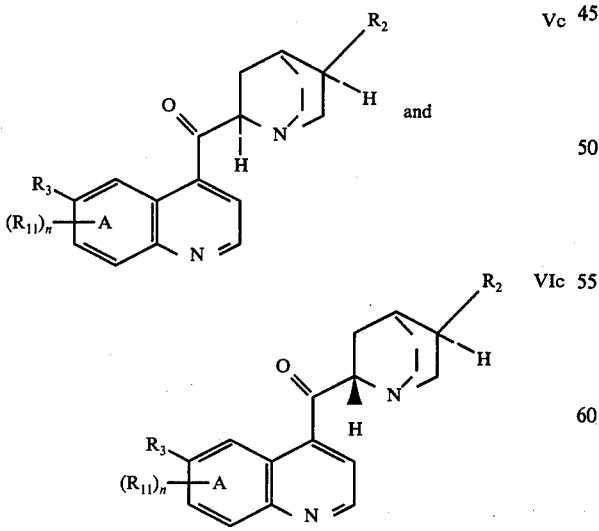

wherein $R_2$, $R_3$, $R_{11}$ and $n$ are as previously described, and pharmaceutically acceptable acid addition salts thereof.

Exemplary of the compounds of Formulas Vc and VIc are:

7-Methoxy-4-[5(R)-ethyl-4(S)-quinuclidin-2(R)-ylcarbonyl]-quinoline [hereinafter referred to as 7'-methoxydihydrocinchoninone], its antipode and racemic analog;

7-Methoxy-4-[5(R)-ethyl-4(S)-quinuclidin-2(S)-ylcarbonyl]-quinoline [hereinafter referred to as 7'-methoxydihydrocinchonidinone], its antipode and racemic analog;

6,7-Dimethoxy-4-[5(R)-ethyl-4(S)-quinuclidin-2(R)-yl-carbonyl]quinoline [hereinafter referred to as 6',7'-dimethoxy-dihydrocinchoninone], its antipode and racemic analog;

6,8-Dimethoxy-4-[5(R)-ethyl-4(S)-quinucidin-2(R)-ylcarbonyl]quinoline, its antipode and racemic analog;

6,7-Dimethoxy-4-[5(R)-ethyl-4(S)-quinuelidin-2(S)-ylcatbonyl]quinoline [hereinafter referred to as a6',7'-dimethoxy-dihydrocinchonidinone], its antipode and racemic analoy;

6,8-Dimethoxy-4-[5(R)-ethyl-4-(S)-quinuclidin-2(S)-ylcarbonyl]quinoline, its antipode and racemic analog;

6-Methyl-4-[5(R)-ethyl-4(S)-quinuclidin-2(R)-ylcarbonyl]-quinoline [hereinafter referred to as 6'-methyldihydrocinchoninone], its antipode and racemic analog;

6-Methyl-4[5(R)-ethyl-4(S)-quinuclidin-2(S)-ylcarbonyl]-quinoline [hereinafter referred to as 6'-methyl-dihydrocinchonidinone], its antipode and racemic analog;

6-Chloro-4-[5(R)-ethyl-4(S)-quinuclidin-2(R)-ylcarbonyl]-quinoline [hereinafter referred to as 6'-chlorodihydrocinchoninone], its antipode and racemic analog;

6-Chloro-4[5(R)-ethyl-4(S)-quinuelidin-2(S)-ylcarbonyl]-quinoline [hereinafter referred to as 6'-chlorodihydrochinchonidinone], its antipode and racemic analog;

7-Chloro-4-[5(R)-ethyl-4(S)-quinuclidin-2(R)-ylcarbonyl]-quinoline [hereinafter referred to as 7'-chlorodihydrocinchoninone], its antipode and racemic analog;

7-Chloro-4-[5(R)-ethyl-4(S)-quinuclidin-2(S)-ylcarbonyl-quinoline [hereinafter referred to as 7'-chlorodihydrocinchonidinone], its antipode and racemic analog;

7-Chloro-4-[5(R)-vinyl-4(S)-quinuclidin-2(R)-ylcarbonyl]-quinoline [hereinafter referred to as 7'-chlorocinchoninone], its antipode and racemic analog;

7-Chloro-4-[5(R)-vinyl-4(S)-quinuclidin-2(S)-ylcarbonyl]-quinoline [hereinafter referred to as 7'-chlorcinchonidinone], its antipode and racemic analog; and the like.

6,7-Methylenedioxy-[5(R)-vinyl-4(S)-quinuelidin-2(R)-ylcarbonyl]-quinoline [hereinafter referred to as 6',7'-methylenedioxy-cinchoninone] its antipode and racemic analog;

6,7-Methylenedioxy-4-[5(R)-vinyl-4(S)-quinuclidin-2(S)-ylcarbonyl]-quinoline [hereinafter referred to as 6',7',-methylenedioxy-cinchonidinone]its antipode and racemic analog;

6,7-Methylenedioxy-4-[5(R)-ethyl-4(S)-quinuclidin-2(R)-ylcarbonyl]-quinoline [hereinafter referred to as 6',7'-methylenedioxy-dihydrocinchoninone], its antipode and racemic analog;

6,7-Methylenedioxy-4-[5(R)-ethyl-4(S)-quinuclidin-2(S)-ylcarbonyl]-quinoline [hereinafter referred to as 6′,7′-methylenedioxydihydrocinchonidinone], its antipode and racemic analog;

6,8-Dichloro-4-[5(R)-ethyl-4(S)-quinuclidin-2(R)-ylcarbonyl]-quinoline [hereinafter referred to as 6′,8′-dichloro-dihydrocinchoninone], its antipode and racemic analog;

6,8-Dichloro-4-[5(R)-ethyl-4(S)-quinuclidin-2(S)-ylcarbonyl]-quinoline [hereinafter referred to as 6′,8′-dichlorodihydrocinchonidinone], its antipode and racemic analog;

6-Chloro-4-[5(R)-vinyl-4(S)-quinuclidin-2(R)-ylcarbonyl]-quinoline [hereinafter referred to as 6′-chlorocinchoninone], its antipode and racemic analog;

6-Chloro-4-[5(R)-vinyl-4(S)-quinuclidin-2(S)-ylcarbonyl]-quinoline [hereinafter referred to as 6′-chlorocinchonidinone], its antipode and racemic analog;

7-Trifluoromethyl-4-[5(R)-ethyl-4(S)-quinuclidin-2(S)-ylcarbonyl]-quinoline [hereinafter referred to as 7′-trifluoromethyl-dihydrocinchonidinone], its antipode and racemic analog;

7-Trifluoromethyl-4-[5(R)-ethyl-4(S)-quinuclidin-2(R)-ylcarbonyl]-quinoline [hereinafter referred to as 7′-trifluoromethyl-dihydrocinchoninone], its antipode and racemic analog;

6,8-Dichloro-4-[5(R)-vinyl-4(S)-quinuclidin-2(R)-ylcarbonyl]-quinoline [hereinafter referred to as 6′,8′-dichlorocinchoninone], its antipode and racemic analog;

6,8-Dichloro-4-[5(R)-vinyl-4(S)-quinuclidin-2(S)-ylcarbonyl]-quinoline [hereinafter referred to as 6′,8′-dichlorocinchonidinone], its antipode and racemic analog. In a still further aspect, the invention relates to compounds of the formulas

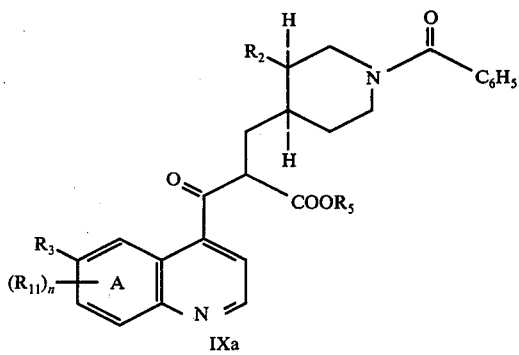

IXa

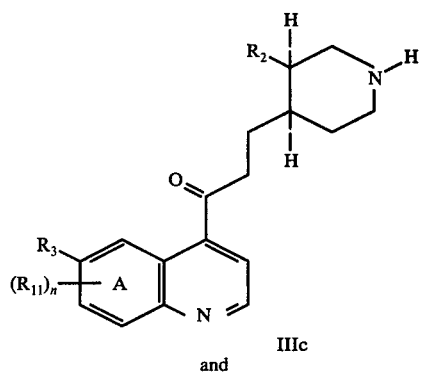

IIIc
and

-continued

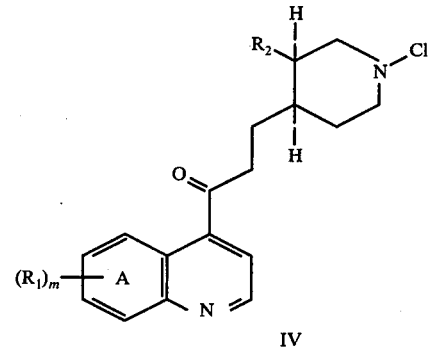

IV wherein $R_1$, $R_2$, $R_3$, $R_5$, $R_{11}$, $m$ and $n$ are as previously described.

Exemplary of the compounds of Formulas IXa, IIIc and IV are:

α-[1-Benzoyl-3(R)-vinyl-4(R)-piperidyl-methyl]-β-oxo-β-(6,7-methylenedioxy-4-quinolyl)propionic acid ethyl ester, its antipode and racemic analog;

α-[1-Benzoyl-3(R)-ethyl-4(R)-piperidylmethyl]-β-oxo-β-(7-methoxy-4-quinolyl)propionic acid ethyl ester, its antipode and racemic analog;

α-[1-Benzoyl-3(R)-ethyl-4(R)-piperidylmethyl]-β-oxo-β-(6,7-dimethoxy-4-quinolyl)propionic acid ethyl ester, its antipode and racemic analog;

α-[1-Benzoyl-3(R)-ethyl-4(R)-piperidylmethyl]-β-oxo-β-(6,8-dimethoxy-4-quinolyl)propionic acid ethyl ester, its antipode and racemic analog;

α-[1-Benzoyl-3(R)-ethyl-4(R)-piperidylmethyl]-β-oxo-β-(6-methyl-4-quinolyl)propionic acid ethyl ester, its antipode and racemic analog;

α-[1-Benzoyl-3(R)-ethyl-4(R)-piperidylmethyl]-β-oxo-β-(6-chloro-4-quinolyl)propionic acid ethyl ester, its antipode and racemic analog;

α-[1-Benzoyl-3(R)-ethyl-4(R)-piperidylmethyl]-β-oxo-β-(7-chloro-4-quinolyl)propionic acid ethyl ester, its antipode and racemic analog;

α-[1-Benzoyl-3(R)-vinyl-4(R)-piperidylmethyl]-β-oxo-β-(7-chloro-4-quinolyl)propionic acid ethyl ester, its antipode and racemic analog;

7-Methoxy-4-[3(R)-ethyl-4(R)-piperidyl)-1-oxopropyl]-quinoline [hereinafter referred to as 7′-methoxy-dihydrocinchotoxine], its antipode and racemic analog;

6,7-Dimethoxy-4-[3-(3(R)-ethyl-4(R)-piperidyl)-1-oxopropyl]-quinoline [hereinafter referred to as 6′,7′-dimethoxydihydrocinchotoxine], its antipode and racemic analog;

6,8-Dimethoxy-4-[3-(3(R)-ethyl-4(R)-piperidyl)-1-oxopropyl]-quinoline, its antipode and racemic analog;

6-Methyl-4-[3-(3R)-ethyl-4(R)-piperidyl)-1-oxopropyl]-quinoline [hereinafter referred to as 6′-methyl-dihydrocinchotoxine], its antipode and racemic analog;

6-Chloro-4-[3-(3R)-ethyl-4(R)-piperidyl)-1-oxopropyl]quinoline [hereinafter referred to as 6′-chlorodihydrocinchotoxine], its antipode and racemic analog;

7-Chloro-4-[3-(3R)-ethyl-4(R)-piperidyl)-1-oxopropyl]-quinoline [hereinafter referred to as 7′-chloro-dihydrocinchotoxine], its antipode and racemic analog;

7-Chloro-4-[3-(3R)-vinyl-4(R)-piperidyl]-1-oxo-propyl]-quinoline [hereinafter referred to as 7'-chlorocinchotoxine], its antipode and racemic analog;

6,7-Methylenedioxy-4[3-(3R)-vinyl-4(R)-piperidyl-1-oxopropyl]-quinoline [hereinafter referred to as 6',7'-methylenedioxycinchotoxine], its antipode and racemic analog;

6-Methoxy-4-[3-(1-chloro-3(R)-ethyl-4(R)-piperidyl)-1-oxopropyl]quinoline [hereinafter referred to as N-chlorodihydroquinotoxine], its antipode and racemic analog;

7-Methoxy-4-[3-(1-chloro-3(R)-ethyl-4(R)-piperidyl)-1-oxopropyl]quinoline [hereinafter referred to as N-chloro-7'-methoxy-dihydrocinchotoxine], its antipode and racemic analog;

6-Methoxy-4-[3-(1-chloro-3(R)-vinyl-4(R)-piperidyl)-1-oxopropyl]quinoline [hereinafter referred to as N-chloroquinotoxine], its antipode and racemic analog;

6,7-Dimethoxy-4-[3-(1-chloro-3(R)-ethyl-4(R)-piperidyl)-1-oxopropyl]quinoline [hereinafter referred to as N-chloro-6',7'-dimethoxy-dihydrocinchotoxine], its antipode and racemic analog;

6,8-Dimethoxy-4-[3-(1-chloro-3-(R)-ethyl-4(R)-piperidyl)-1-oxopropyl]quinoline, its antipode and racemic analog;

6-Methyl-4-[3-(1-chloro-3(R)-ethyl-4(R)-piperidyl)-1-oxopropyl]quinoline [hereinafter referred to as N-chloro-6'-methyl-dihydrocinchotoxine], its antipode and racemic analog;

6,7-Methylenedioxy-4-[3-(1-chloro-3(R)-vinyl-4(R)-piperidyl)-1-oxo-propyl]quinoline [hereinafter referred to as N-chloro-6,7-methylenedioxyqinotoxine], its antipode and racemic analog;

6-Chloro-4-[3-(1-chloro-3(R)-ethyl-4(R)-piperidyl)-1-oxopropyl]quinoline [hereinafter referred to as N-chloro-6'-chloro-dihydrocinchotoxine], its antipode and racemic analog;

7-Chloro-4-[3-(1-chloro-3(R)-vinyl-4(R)-piperidyl)-1-oxopropyl]quinoline [hereinafter referred to as N-chloro-7'-chloro-cinchotoxine], its antipode and racemic analog;

7-Chloro-4-[3-(1-chloro-3(R)-ethyl-4(R)-piperidyl)-1-oxopropyl]-quinoline [hereinafter referred to as N-chloro-7'-chloro-dihydrocinchotoxine], its antipode and racemic analog.

Preferred compounds of Formulas Ic, IIc, IIIc, Vc, VIc and IXa are those wherein the fused benzo ring (hereinafter referred to as ring A) is substituted thusly:

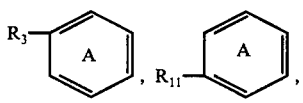

Preferred compounds of Formula IV are those wherein ring A is

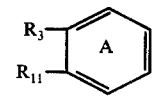

Also included in the purview of the invention are compounds of Formulas Ic, IIc, Vc, VIc, IXa and IIIc, wherein $R_{11}$ is hydrogen; $R_3$ is methoxy; and $R_2$ is selected from the group consisting of methyl, $C_3$–$C_7$ lower alkyl and $C_3$–$C_7$ lower alkenyl. Respectively, these compounds have the same utility as the compounds of Formulas Ic, IIc, Vc, VIc, IXa and IIIc.

The corresponding compounds of Formulas Ic and IIc above are characterized by the formulas

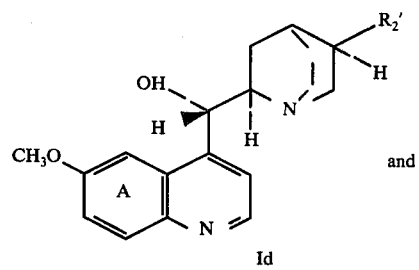

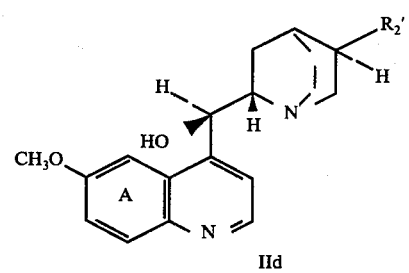

wherein $R_2'$ is selected from the group consisting of methyl, $C_3$–$C_7$ lower alkyl and $C_3$–$C_7$ lower alkenyl, the corresponding compounds of the Formulas Vc, VIc, IXa and IIIc wherein $R_{11}$ is hydrogen; $R_3$ is methoxy; $R_2$ is methyl $C_3$–$C_7$-lower alkyl and $C_3$–$C_7$ lower alkenyl can be similarly characterized, and pharmaceutically acceptable acid addition salts thereof.

Exemplary of such compounds are 6-methoxy-α(S)-[5(R)-propyl-4(S)-quinuclidin-2(R)-yl]-4-quinolinemethanol and racemic analog; 6-methoxy-α(R)-[5(R)-allyl-4(S)-quinuclidin-2(S)-yl]-4-quinolinemethanol and racemic analog; and the like.

The compounds of Formulas Ic, IIc, Id, IId, Vc and VIc and their pharmaceutically acceptable acid addition salts possess antimalarial and antiarrhythmic properties and are therefore useful as antimalarial and antiarrhythmic agents. Their pharmacologically useful antiarrhythmic activity is demonstrated in warm-blooded animals utilzing standard procedures, for example, the test compound is administered-to prepared mongrel dogs. The chest cavity of the experimental animal previously anesthetized using a combination of sodium barbitol, 300 mg/kg. and pentobarbitol, 15 mg/kg., i.v., is opened up through the third right interspace under artificial respiration and the pericardium is cut and sutured to the wall of the thorax so as to maintain the heart in a pericardial cradle throughout the course of the test procedure. Arterial pressure is monitored by inserting a polyethylene cannula into the aorta via the left carotid artery and is measured with an appropriate Statham pressure transducer. During the course of the experiment, electrical activity of the heart is viewed both on an oscilloscope and recorded on a Sanborn polyviso using standard ECG lead II. The heart is also observed visually. The antiarrhythmic assay of the test drug is undertaken using a modification of the method of Scherf and Chick, Circulation, 3, 764-769 (1951). A dripping of 1 percent solution of acetylcholine is applied to the sinus node and the atrium is irritated by pinching with a pair of forceps. This procedure produces a continuous atrial arrhythmia which mostly consists of atrial fibrillation. Since hypokalemia produces a susceptibility to atrial fibrillation (Leveque, Arch. Int. Pharmacodyn, 140, 297-307, 1964), 2 units/kg. of insulin is administered 30 minutes before the start of the acetylcholine drip. Once atrial fibrillation is established, there is a ten-minute waiting period before the test drug is administered. The test drugs are administered intravenously at the rate of 1 mg/kg/minute until normal sinus rhythm appears or until 30 mg/kg. of drug is administered.

When racemic 7'-methoxy-dihydrocinchonidinone is utilized as the test substance at a dosage of about 4.4 mg/kg., i.v., an antifibrillatory effect is observed for more than 60 minutes.

The pharmacologically useful antimalarial activity of the aforementioned compounds is demonstrated in warm-blooded animals using standard procedures, for example, the test substance is administered to albino mice in variable amounts. Albino mice are inoculated with about 10 million red cells infected with *P. Bergei*. Treatment is started on the first day after inoculation, and the drug is administered "per os" during 4 consecutive days. On the seventh day of infection, smears are made, stained with giemsa and microscopically examined for P. Berghei.

When racemic 7'-methoxy-dihydrocinchonidine dihydrochloride and racemic 7'-methoxy-dihydrocinchonine dihydrochloride are utilized as the test substance at dosages in the range of 125 mg/kg. to about 250 mg/kg., the microscopical examination of the blood smears is free of *P. Berghei* (negative). The compounds of Formulas Ic, IIc, Vc and VIc and the pharmaceutically acceptable acid addition salts have effects qualitatively regular, for example, to those of quinine and quinidine of known therapeutic uses and properties. Thus, the compouns of the invention demonstrate a pattern of activity associated with antimalarials and antiarrhythmics of known efficacy and safety.

The compounds of Formulas Ic, IIc, Id, IId, Vc, and VIc form acid addition salts and such salts are also within the scoe of this invention. Thus, the aforementioned compounds form pharmaceutically acceptable addition salts with, for example, both pharmaceutically acceptable organic and inorganic acids, such as acetic acid, succinic acid, formic acid, methanesulfonic acid, p-toluene-sulfonic acid, hydrochloric acid, nitric acid, phosphoric acid, sulfuric acid and the like.

The products of the invention can be incorporated into standard pharmaceutical dosage forms, for example, they are useful for oral or parenteral application with the usual pharmaceutical adjuvant materials, e.g., organic or inorganic inert carrier materials such as water, gelatin, lactose, starch, magnesium stearate, talc, vegetable oils, gums, polyalkylene-glycols, and the like. The pharmaceutical preparations can be employed in a solid form, e.g., as tablets, troches, suppositories, capsules, or in liquid form, e.g., as solutions, suspensions or emulsions. The pharmaceutical adjuvant material can include preservatives, stabilizers, wetting or emulsifying agents, salts to change the osmotic pressure or to act as buffers. They can also contain other therapeutically active materials.

Furthermore, the compounds of the Formulas Ic, IIc, Id and IId can be utilized as flavoring agents in beverages in the same manner as quinine is used for this purpose.

The quantity of active medicament which is present in any of the above-described dosage forms is variable. The frequency with which any such dosage form will be administered will vary, depending upon the quantity of active medicament present therein and the needs and requirements of the pharmacological situation.

Due to the possible different spatial arrangements of their atoms, it is to be understood that the compounds of this invention may be obtained in more than one possible stereoisomeric form. The novel compounds, as described and claimed, are intended to embrace all such isomeric forms. Accordingly, the examples included herein are to be understood as illustrative of particular mixtures of isomers or single isomers and not as limitations upon the scope of the invention. All temperatures are in degrees centigrade, unless otherwise mentioned.

EXAMPLE 1

Preparation of Dihydroquinidinone

To a solution containing 1.5 g. of dihydroquinotoxine in 120 ml. of methylene chloride were added 2.5 ml. of 17% aqueous NaOCl solution and the mixture was stirred 16 hours at 20°, under nitrogen. The organic phase was separated, washed once with water, dried over anhydrous sodium sulfate, and evaporated. The crude N-chloro-dihydroquinotoxine (1.65 g.) was dissolved in 10 ml. of methylene chloride and added dropwise to 80 ml. of 100% phosphoric acid which was stirred vigorously; the viscous mixture was stirred at 20° for 4 hours. The mixture was cooled and made alkaline to a pH $\approx$ 10 with 6N aqueous sodium hydroxide the alkaline aqueous phase was extracted thoroughly with chloroform, which was dried over anhydrous sodium sulfate, and evaporated to dryness. The crude product (1.49 g.) was chromotographed on a column of 50 g. of neutral alumina, activity II; elution with methylene chloride yielded 1.1 g. (73%) of an amorphous mixture of dihydroquinidinone and dihydroquininone which was crystallized from ethanol to yield 930 mg. of dihydroquinidinone having a melting point of 102°-104° after recrystallization from ether; $[\alpha]_D^{25} + 71°$ (c. 1.1, ethanol; after equilibration in ethanolic solution for 18 hours at 20°).

EXAMPLE 2

Preparation of Racemic dihydroquininone and racemic dihydroquinidinone from racemic dihydroquniotoxine To a solution containing 14.8 g. of racemic dihydroquinotoxine in 100 ml. of chloroform were added 26 ml. of 17% aqueous sodium hypochlorite solution, and the mixture was agitated under nitrogen at 20° for 16 hours. The aqueous phase was separated and washed with methylene chloride. The organic phases were combined, washed with water, dried over anhydrous sodium sulfate and evaporated to dryness.

The crude racemic N-chloro-dihydroquinotoxine (about 15 g.) was dissolved in about 20 ml. of methylene chloride and the concentrated solution was added dropwise to 120 ml. of 100% phosphoric acid which was cooled in an ice-bath and vigorously stirred for 4 hours; the cooled solution was made alkaline with 6N aqueous sodium hydroxide and extracted thoroughly with ether. The ethereal phase was dried over anhydrous potassium carbonate and evaporated to dryness.

The crude product (14 g.) was chromatographed on 500 g. of alumina, activity II. Elution with methylene chloride containing 0 to 1% of methanol yielded 10.1 g. of pure, crystalline mixture of racemic dihydroquininone and racemic dihydroquinidinone (68% yield from dihydroquinotoxine). Crystallization from petroleun ether yielded 8.09 g. of crystals in three crops. The first crop having a melting point of 89°–95° was recrystallized four times from petroleum ether to yield racemic dihydroquininone having a melting point of 100°–104°.

Recrystallization of the third crop, having a melting point of 80°–82°, from petroluen ether yielded about a 1:1 mixture of racemic dihydroquininone and racemic dihydroquinidinone having a melting point of 80°–83°.

EXAMPLE 3

Preparation of Quinidinone from Quinotoxine

To a solution containing 1.804 g. of quinotoxine in 35 ml. of methylene chloride were added 6.4 ml. of about a 17% aqueous sodium hypochlorite solution, and the mixture was stirred under nitrogen for 2 1/2 hours at 20°. The organic layer was separated, washed with water, dried over anhydrous sodium sulfate and evaporated to dryness. The crude N-chloroquinotoxine (1.927 g.) was dissolved in about 6 ml. of methylene chlorideacetic acid 4:1 and added dropwise with stirring to 10 ml. of 99.5% phosphoric acid. The resulting viscous mixture was stirred at 0°–20° for 2 hours. The reaction mixture was poured into 50 ml. of water. The aqueous phase was made alkaline with 6N sodium hydroxide and the temperature was allowed to rise to about 40°. After 10 minutes, the aqueous alkaline phase was extracted thoroughly with methylene chloride; the organic phase was washed with water, dried over anhydrous sodium sulfate, and evaporated to dryness. The crude product (1.714 g.) was chromatographed through 17 g. of neutral alumina, activity II; elution with methylene chloride yielded 1.178 g. (66%) of a mixture of quinidinone and quininone. Crystallization from ether yielded 915 mg. (51%) of quinidinone which after recrystallization from ether had a melting point of 98°–101°; $[\alpha]_D^{25}$ + 72.6° (c. 0.99, ethanol; after equilibration in ethanolic solution for 18 hours at 20°).

EXAMPLE 4

Preparation of Racemic 7'-Methoxy-dihydrocinchotoxine from cis 1-benzoyl-3-ethyl-4-piperidinepropionic aicd ethyl ester and 7-methoxy-4-carbethoxy-quinoline A solution containing 25.4 g. of cis 1-benzoyl-3-ethyl-4-piperidinepropionic acid ethyl ester in 250 ml. of dry tetrahydrofuran was added dropwise (30 min.) to a gently refluxing mixture of 26.9 g. of potassium t-butoxide and 25.8 g. of 7-methoxy-4-carbethoxyquinoline in 400 ml. of dry tetrahydrofuran, in an atmosphere of dry nitrogen. The mixture was heated under gentle reflux for two hours, and the solvent was removed under reduced pressure. The residue was dissolved in 300 ml. of 0.5N sodium hydroxide, and was washed with benzene. The alkaline aqueous phase containing α-cis(1-benzoyl-3-ethyl-4-piperidylmethyl)-β-oxo-β-(7-methoxy-4-quinolyl)propionic acid ethyl ester was acidified so that a 6N aqueous hydrochloric acid solution was obtained, and the solution was heated under reflux for 21 hours. The cooled reaction mixture was made alkaline with 6N sodium hydroxide, and extracted thoroughly with ether. The ethereal extracts were dried over anhydrous potassium carbonate and concentrated to dryness.

The crude product (21.0 g.) was dissolved in a small volume of acetone and added to a solution containing 14.5 g. of dibenzoyl-d-tartaric acid in acetone. The precipitate was separated by filtration, the free bases of the mother liquors were purified by preparative tlc to yield racemic 7'-methoxy-dihydrocinechltoxine. A sample of the neutral dibenzoyl-d-tartarate was recrystallized from methanol and had a melting point of 174°–175.5°. The free base dl-7'-methoxy-dihydrocinchotoxine was obtained as a yellow oil.

EXAMPLE 5

Preparation of 7'-Methoxy-dihydrocinchotoxine from N-benzoylhomocinchlolipone ethyl ester and 7-methoxy-4-carbethoxy quinoline A solution containing 4.14 g. of N-benzoylhomocincholoipone ethyl ester in 40 ml. of dry tetrahydrofuran was added dropwise (20 min.) to a gently refluxing mixture of 4.98 g. of potassium t-butoxide and 4.74 g. of 7-methoxy-4-carbethoxyquinoline in 90 ml. of dry tetrahydrofuran in an atmosphere of dry nitrogen. The mixture was heated under gentle reflux for three hours, then the solvent was removed by distillation under vacuum, and the cooled residue dissolved in 100 ml. of 0.5N sodium hydroxide. The alkaline phase was washed with benzene and the benzene phases washed with 0.5N sodium hydroxide. The combined aqueous phases containing α-[1-benzoyl-3(R)-ethyl-4(R)piperidylmethyl]-β-oxo-β-(7-methoxy-4-quinolyl propionic acid ethyl ester were acidified so that a 6N hydrochloric acid solution was obtained, and then heated under gentle reflux for 17 hours. The cooled reaction mixture was made alkaline with 6N sodium hydroxide and thoroughly extracted with ether. The ethereal extracts were dried over anhydrous potassium carbonate and evaporated to dryness. The crude product (3.30 g.) was dissolved in a small volume of acetone, and 1.7 g. of dibenzoyl-d-tartaric acid as a concentrated solution in acetone was added. Crystallization yielded 4.11 g. (54%) of 7'-methoxy-dihydrocinchotoxine as its neutral dibenzoyl-d-tartarate; having a melting point of 177°–179° after recrystallization from chloroformmethanol; $[\alpha]_D^{26}$ −39.6° [c 0.5, ethanol-chloroform (1:2)].

EXAMPLE 6

Preparation of 7'-Methoxy-dihydrocinchoninone and 7'-methoxy-dihydrocinchonidinone from 7'-methoxy-dihydrocinchotoxine To a solution containing 2.65 g. of 7'-methoxy-dihydrocinchotoxine in 100 ml. of chloroform were added 5 ml. of about a 17% aqueous sodium hypochlorite soiution. The resulting mixture was stirred at 20° for 16 hours. The organic phase was separated, washed with water, dried over anhydrous sodium sulfate and evaporated. The crude N-chloro-7'-methoxy-dihydrocinchotoxine was dissolved in a minimal amount of chloroform and added dropwise to 15 ml. of 100% phosphoric acid with vigorous stirring. The resulting viscous mixture was stirred at 20° for 4 hours. Thereafter, it was made alkaline with 6N potassium hydroxide and the temperature of the alkaline phase was allowed to reach about 40°. After 10 minutes, the aqueous phase was extracted thoroughly with ether. The ethereal phase was dried over anhydrous potassium carbonate, and concentrated to dryness. The crude product (2.49 g.) was chromatographed on a column of 75 g. of neutral alumina, activity II; elution with methylene chloride yielded 1.49 g. (56%) of a mixture of 7'-methoxy-dihydrocinchoninone and 7'-methoxy-dihydrocinchonidinone having a melting point of 103°–108° after recrystallization from petroleum ether; and a specific rotation of $[\alpha]_D^{25} + 16°$ (c 0.27, ethanol; after equilbration in ethanolic solution for 18 hours at 20°).

In the like manner, the following analogs can be prepared: A mixture of 7-chloro-4-[5(R)- ethyl-4(S)-quniuclidin-2(R)-ylcarbonyl]-quinoline and 7-chloro-4-[5(R)-ethyl-4(S)-quinuclidin-2(S)-ylcarbonyl]-quinoline, which is amorphous; its antipode, which is amorphous: and racemate thereof, having a m.p. of 124°–127°;

A mixture of 7-chloro-4-[5(R)-vinyl-4(S)-quinuclidin-2(S)-ylcarbonyl]-quinoline and 7-chloro-4-[5(R)-vinyl-4(S)-quinuclidin-2(S)-ylcarbonyl]-quinoline, which is amorphous;

A mixture of racemic 7-trifluoromethyl-4-[5(R)-ethyl-4(S)-quinuclidin-2(R)-ylcarbonyl]-quinoline and racemic 7-trifuloromethyl-4-[5(R)-ethyl-4(S)-quinuclidin-2(S)-ylcarbonyl]-quinoline: m.p. 106°–111°.

EXAMPLE 7

Preparation of Racemic 7'-methoxy-dihydrocinchonidinone and racemic 7'-methoxy-dihydrocinchoninone from racemic 7'-methoxy-dihydrocinchotoxine To a solution containing 20.6 g. of racemic 7'-methoxy-dihydrocinchotoxine in 150 ml. of chloroform were added 55 ml. of about a 17% aqueous sodium hypochlorite solution, and the mixture was agitated for 16 hours at 20°. The organic phase was separated, washed with water, dried over anhydrous sodium sulfate and evaporated to dryness. The crude racemic N-chloro-7'-methoxy-dihydrocinchotoxine was dissolved in a minimum volume of chloroform and added dropwise to 150 ml. of concentrated phosphoric acid at 20° with vigorous stirring. The resulting viscous mixture was stirred for 2 hours. The solution was cooled with ice, diluted with water, and made alkaline with 6N sodium hydroxide. During neutralization the temperature was allowed to reach about 40°. After about 10 minutes, the alkaline aqueous phase was extracted thoroughly with ether and the ethereal phase was dired over anhydrous potassium carbonate and evaporated to dryness. The crude, crystalline product (20.4 g.) was dissolved in petroleum ether, leaving an insoluble, tarry residue of 3.4 g. Crystallization from the same solvent yielded 9.49 g. of racemic 7'-methoxy-dihydrocinchonidinone and 7.52 g. of an amorphous mixture of racemic 7'-methoxy-dihydrocinchoninone and racemic 7'-methoxy-dihydrocinchonidinone (total yield 82%). After 2 recrystallizations from petroleum ether, racemic 7'-methoxy-dihydrocinchonidinone had a melting point of 115°–118°.

EXAMPLE 8

Preparation of Dihydroquinidine from dihydroquinidinone

To a solution containing 2.0 g. of dihydroquinidinone in 150 ml. of dry toluene, stirred at 20° in an atmosphere of cry nitrogen, were added dropwise 4.8 ml. of a 25% solution of diisobutyl aluminum hydride in toluene. As soon as all the ketone was consumed, the reaction was quenched by the addition of 3 ml. of water-methanol (1:1). The aluminum hydroxide which precipitated was separated by filtration and was washed thoroughly with benzene and methanol. The combined filtrates were evaporated to dryness. Crystallization of the residue from ethanol yielded 1.90 g. of dihydroquinidine (94% yield) in three crops which after recrystallization from ethanol had a melting point of 168 –169°; $[\alpha]_D^{22} + 227.9°$ (c 0.896, ethanol).

EXAMPLE 9

Preparation of Dihydroquinidine and dihydroquinine from a mixture of dihydroquinidinone and dihydroquininone A solution containing 1.25 g. of dihydroquinidinone in 50 ml. of benzene containing 0.5 ml. of methanol was maintained at 20° for 2½ days under nitrogen. The solution was evaporated to complete dryness under vacuum, and the residue was redissolved in benzene and again evaporated to dryness. The resulting oily residue was dissolved in 50 ml. of dry benzene, and 3 ml. of a 25% solution of di-isobutyl aluminum hydride in toluene were added dropwise with stirring under an atomsphere of dry nitrogen. The reaction was quenched after about 30 minutes by adding 10 ml. of water-methanol (1:1), and the mixture was stirred vigorously for 30 minutes. The benzene layer was decanted. The aqueous aluminum suspension was washed several times with benzene and the combined benzene phases were dried over anhydrous magnesium sulfate and evaporated to dryness. The crude product (1.25 g. of colorless foam) was a practically pure mixture of dihydroquinidine and dyhydroquinine (about 1:1) as determined by thin layer chromatography; and a specific rotation $[\alpha]_D^{24,5} + 62.2°$ (c 1.64, ethanol). Crystallization from ethanol yielded 490 mg. of pure dihydroquinidine having a melting point of 167°–169°. Chromatographic separation from mother liquors gave 550 mp of dihydroquinine, m.p. 168°–170°, $[\alpha]_D^{29} - 137.5°$.

EXAMPLE 10

Preparation of racemic dihydroquinine from racemic dihydroquininone

To a solution containing 1.0 g. of racemic dihydroquininone in 100 ml. of dry benzene were added dropwise 2.5 ml. of a 25% solution of di-isobutyl aluminum hydride in toluene with stirring under an atmosphere of dry nitrogen. After about 30 minutes, the reaction was quenched by the addition of 2 ml. of methanol-water (1:1). The alumina which precipitated was separated by filtration, washed thoroughly with methanol, and the filtrate was evaporated to dryness. Crystallization of the crude product (1.003 g.) from acetone yielded 718 mg. of racemic dihydroquinine as its monohydrate, which after recrystallization from acetone had a melting point of 174°–177°.

EXAMPLE 11

Preparation of Racemic dihydroquinine and racemic dihydroquinidine from a mixture of racemic dihydroquininone and racemic dihydroquinidinone The reduction of 5.06 g. of a crystalline mixture of racemic dihydroquininone and dihydroquinidinone (melting point of 76°-89°) was carried out in dry benzene with di-isobutyl aluminum hydride according to the procedure described in Example 8. the methanol extracts (3.87 g.) were crystallized from acetone to yield 3.14 g. (61%) of racemic dihydroquinine monohydrate ins three crops. The benzene extracts (1.54 g.) were crystallized from a concentrated solution in ethanol to yield 579 mg. (11%) of racemic dihydroquinidine in four crops. Racemic dihydroquinidine: after recrystallization from ethanol had a melting point of 152°-154.5°.

EXAMPLE 12

Preparation of Racemic dihydroquinidine sulfate

To 2.02 g. of d,1-dihydroquinidine in 25 ml. of absolute ethanol were first added 6.2 ml. of 1N aqueous sulfuric acid, followed by 5 ml. of water. The sulfate (2.03 g.) crystallized after the volume was evaporated to 20 ml. After drying at 80°/0.01 mm for 70 hours, the d,1-dihydroquinidine $SO_4$ contained ¾ mole of water and had a melting point of 208°-211°.

EXAMPLE 13

Preparation of Quinidine from quinidinone

To a solution containing 1.00 g. of quinidinone in 40 ml. of dry benzene were added dropwise 2.4 ml. of a 25% solution of di-isobutyl aluminum hydride in toluene. After stirring at 20° under an atmosphere of dry nitrogen, 10 ml. of water was added. The benzene layer was separated, dried over anhydrous magnesium sulfate, and evaporated to dryness. The crude, crystalline product (0.890 g.) was recrystallized from ethanol to yield 0.646 g. of crystallin quinidine having a melting point of 169°-171°; $[\alpha]_D^{25}$ + 264.3 (c 0.98, ethanol).

In the like manner, the following can be prepared: 7-chloro-α(S)-[5(R)-vinyl-4(S)-quinuclidin-2(R)-yl]-4-quinoline-methanol which crystallized from ethanol-acetone has a melting point of 247°-250°, $[\alpha]_D^{25}$ + 196° (c 0.88, ethanol-methylene chloride 4:1); and 7-chloro-α(R)-[5(R)-vinyl-4(S)-quinuclidin-2(S)-yl]-4-quinoline-methanol which crystallized from acetone-ether, has a melting point of 165°-169°, $[\alpha]_D^{25}$ − 67° (c 0.90, ethanol);

7-Chloro-α(S)-[5(R)-ethyl-4(S)-quinuclidin-2(R)-yl]-4-quinolinemethanol which crystallized from ethanol-acetone has a melting point of 278°-279° $[\alpha]_D^{25}$ + 159.7° (ethanol acidic acid 9:1).

6-Chloro-α(S)-[5(R)-ethyl-4(S)-quinuclidin-2(R)-yl]-4-quinolinemethanol, m.p. 98°-100°.

6-Chloro-α(R)-[5(R)-ethyl-4(S)-quinuclidin-2(S)-yl]-4-quinolinemethanol, m.p. 196°-198°.

Antipode of 7-chloro-α(S)-[5(R)-ethyl-4(S)-quinuclidin-2(R)-yl]-4-quinolinemethanol, m.p. 278°-280°, and racemic analog, m.p. 252°-253°.

7-Chloro-α(R)-[5(R)-ethyl-4(S)-quinuclidin-2(S)-yl]-4-quinolinemethanol, m.p. 218°-220°, antipode, m.p. 224°-225°, and racemic analog, m.p. 192°-193°.

6-Chloro-α(S)-[5(R)-vinyl-4(S)-quinuclidin-2(R)-yl]-4-quinolinemethanol, m.p. 154°-155°.

6-Chloro-α(R)-[5(R)-vinyl-4(S)-quinuclidin-2(S)-yl]-4-quinolinemethanol, m.p. 193°-194°.

6,8-Dichloro-α(S)-[5(R)-vinyl-4(S)-quinuclidin-2(R)-yl]-4-quinolinemethanol (dihydrochlorid, m.p. 250° dec.)

6,8-Dichloro-α(R)-[5(R)-vinyl-4(S)-quinuclindin-2(S)-yl]-4-quinolinemethanol, m.p. 105°-108°.

Racemic 7-trifluoromethyl-α(S)- [5(R)-ethyl-4(S)-quinuclidin-2(R)-yl]-4-quinolinemethanol, m.p. 218°-219.5°.

Racemic 7-trifluoromethyl-α(R)-[5(R)-ethyl-4(S)-quinuclidin-2(S)-yl]-4-quinolinemethanol, m.p. 175°-176°.

7-Trifluoromethyl-α(S)-[5(R)-vinyl-4(S)-quinuclidin-2(R)-yl]-4-quinolinemethanol, M.P. 228°-229°°.

7-Trifluoromethyl-α(R)-[5(R)-vinyl-4-(S)-quinuclidin-2-(S)-yl]-4-quinolinemethanol (dihydrochloride, m.p. 211°-215°).

7-Trifluoromethyl-α(S)-[5(R)-ethyl-4(S)-quinuclidin-2(R) -yl]-4-quinolinemethanol, m.p. 227°-230 °.

7-Trifluoromethyl-α(R)-[5(R)-ethyl-4(S)-quinuclidin-2 (S)-yl]-4quinolinemethanol, m.p. 163°-164°.

5-Trifluoromethyl-α(S)-[5(R)-vinyl-4(S)-quinuclidin-2(R)-yl]-4-quinolinemethanol.

5-Trifluoromethyl-α(R)-[5(R)-vinyl-4(S)-quinuclidin-2(S)-yl]-4-quinolinemethanol.

6-Trifluoromethyl-α(S)-[5(R)-vinyl-4(S)-quinuclidin-2(R)-yl]-4-quinolinemethanol.

6-Trifluoromethyl-α(R)-[5 (R)-vinyl-4(S)-quinuclidin-2(S)-yl]-4-quinolinemethanol.

EXAMPLE 14

Preparation of 7'-Methoxy-dihydrocinchonine and 7'-methoxy-dihydrocinchonidine from a mixture of 7'-methoxy-dihydrocinchoninone and 7'-methoxy-dihydrocinchonidinone To a solution containing 1.46g. of a mixture of 7'-methoxy-dihydrocinchoninone and 7'-methoxy-dihydrocinchonidinone in 50 ml. of dry benzene, stirred under an atmosphere of dry nitrogen at 20°, were added dropwise 3.75 ml. of a 25% solution of di-isobutyl aluminum hydride in toluene. When all the ketone was consumed, 5ml. of 50% aqueous methanol were added. The alumina which precipitated was separated by filtration, and washed thoroughly with benzene. The combined filtrates were dried over anhydrous sodium sulfate and evaporated to dryness. The crude product was triturated with acetone, and crystallization yielded 7'-methoxy-dihydrocinchonine. After recrystallizations from chloroform-petroleum ether, 7'-methoxy-dihydrocinchonine had a melting point of 231°-233°; $[\alpha]_D^{25}$ + 169.5°(c 1.00, ethanol). From the mother liquors, 7'-methoxy-dihydrocinchonidine was obtained by fractional crystallization from acetone. After recrystallization, 7'-methoxy-dihydrocinchonidine had a melting point of 162°-165°; $[\alpha]_D^{25}$ −80.3°(c 0.98, ethanol).

EXAMPLE 15

Preparation of Racemic 7'-methoxy-dihydrocinchonidine from racemic 7'-methoxy-dihydrocinchonidinone To a solution containing 2.32g. of racemic 7'-methoxy-dihydrocinchonidinone (melting point 112°-116°) in 50ml. of dry benzene was added dropwise 6.5 ml. of a 25% solution of di-isobutyl aluminum hydride in toluene at 20° under an atmosphere of dry nitrogen. After stirring for about 30 minutes at 20°, 8 ml. of 50% aqueous methanol were added. The alumina which precipitated was separated by filtration and washed thoroughly with benzene. The filtrate was dried over anhydrous sodium sulfate and concentrated to dryness. The residue was triturated with etherand 1.78 g. of crystalline racemic 7'-methoxy-dihydro-cinchonidine having a melting point of 155°-157° were collected.

EXAMPLE 16

Preparation of Racemic 7'-methoxy-dihydrocinchonine and racemic 7'-methoxy-dihydrocinchonidine from a mixture of racemic 7'-methoxy-dihydrocinchoninone and 7'-methoxy-dihydrocinchonidinone To a solution containing 2.52 g. of an amorphous mixture of racemic 7'-methoxy-dihydrocinchoninone and racemic 7'-methoxy-dihydrocinchonidinone in 50 ml. of dry benzene, were added dropwise 7.2 ml. of a 25% solution of di-isobutyl aluminum hydride in toluene at 20° under an atmosphere of dry nitrogen. After stirring for about 30 minutes at 20°, 8 ml. of 50% aqueous methanol were added, the alumina which precipitated was separated by filtration and washed thoroughly with benzene. The filtrate was dried over anhydrous sodium sulfate and concentrated to dryness. The residue was triturated with acetone, and 1.01 g. of isomer, i.e., racemic 7'-methoxy-dihydrocinchonine, were separated. It had a melting point of 217°–219° after recrystallization from chloroform-acetone. From the mother liquors, 0.63 g. (25%) of the lower melting racemic 7'-methoxy-dihydrocinchonidine was isolated.

EXAMPLE 17

Mixture of 6',7'-Dimethoxy-dihydrocinchoninone and 6',7'-dimethoxy-dihydrocinchonidinone from 6',7'-dimethoxy-dihydrocinchotoxine To a solution containing 1.42 g. of 6',7'-dimethoxy-dihydrocinchotoxine in 50 ml. of chloroform was added 3.5 ml. of about 17% aqueous sodium hypochlorite, and the mixture was stirred at 20° for 90 minutes. The organic phase was separated, washed with water, dried over anhydrous sodium sulfate and concentrated to a volume of 10 ml. The solution containing 6,7-dimethoxy-4[3-(1-chloro-3(R)-ethyl-4(R)-piperidyl)-1-oxopropyl]-quinoline was added dropwise to 10 ml. of 100% phosphoric acid, and the viscous mixture was stirred at 20° for 5 hours. The mixture was diluted with water, made alkaline with 6N potassium hydroxide while allowing the alkaline phase to reach about 40°, and extracted thoroughly with ether. The ethereal phase was dried over anhydrous potassium carbonate and concentrated to dryness. The crude product was purified on preparative tlc plates [chloroform-triethylamine (9:1)], to yield .794 g. of a pure, amorphous mixture (about 1:1) of 6',7'-dimethoxy-dihydrocinchoninone and 6',7'-dimethoxy-dihydrocinchonidinone.

EXAMPLE 18

6',7'-Dimethoxy-dihydrocinchonine and 6',7'-dimethoxy-dihydrocinchonidine from a mixture of 6',7'-dimethoxy-dihydrocinchoninone and 6',7'-dimethoxy-dihydrocinchonidinone To a solution containing 0.745 g. of a mixture of 6',7'-dimethoxy-dihydrocinchoninone and 6',7'-dimethoxy-dihydrocinchonidinone in 20 ml. of dry benzene, which was stirred in an atmosphere of dry nitrogen at 20°, were added dropwise 1.5 ml. of 25% di-isobutyl aluminum hydride in toluene. After about 60 minutes, 5 ml. of water-methanol (2:3) mixture was added. The precipitated alumina was separated by filtration and washed thoroughly with benzene. The combined filtrates were dried over anhydrous sodium sulfate and evaporated to dryness. The crude product was separated by preparative tlc (chloroform-triethylamine-methanol = 85:10:5) into the two isomers 6',7'-dimethoxy-dihydrocinchonine and 6',7'-dimethoxy -dihydrocinchonidine. The less polar 6',7'-dimethoxy-dihydrocinchonine was crystallized from ether; and had a melting point of 116°–118° after several recrystallizations from acetone; $[\alpha]_D^{25}$ + 182.2° (c 0.95,ethanol). The more polar 6',7'-dimethoxy-dihydrocinchonidine could not be crystallized; $[\alpha]_D^{25}$ -87.3° (c 0.68, ethanol).

EXAMPLE 19

Preparation of Racemic 6', 7'-Dimethoxydihydrocinchonidinone and Racemic 6',7'-Dimethoxydihydrocinchroninone from Racemic 6',7'-Dimethoxydihydrocinchotoxine To a solution containing 14.5 g. of racemic 6',7'-dimethoxydihydrocinchotoxine in 200 ml. of dichloromethane was added 25 ml. of about a 17% aqueous sodium hypochlorite, and the mixture was stirred vigorously for 60 minutes. The organic phase was separated, washed with water, dried over anhydrous sodium sulfate, and evaporated to a volume of about 20 ml. This solution containing the chloramine was added dropwise to 60 ml. of 99.5% phosphoric acid. The cosolvent was evaporated and the viscous mixture stirred at 20° for 4 hours. The mixture was diluted with water and made alkaline with 6N sodium hydroxide. The alkaline phase was allowed to reach about 40°, and was extracted with ether. The ethereal phase was dried over anhydrous potassium carbonate and concentrated to dryness. The product (12.8 g.) was absorbed on 100 g. of neutral alumina, activity II, Elution with benzene and dichloromethane yielded 9.2 g. (65%) of an amorphous mixture comprising racemic 6',7'-dimethoxydihydrocinchonidinone and racemic 6',7'-dimethoxydihydrocinchroninone.

EXAMPLE 20

Preparation of Racemic 6',7'-Dimethoxydihydrocinchronidine and Racemic 6',7'-Dimethoxydihydrocinchronine from a mixture of racemic 6',7'-Dimethoxydihydrocinchronidinone and Racemic 6',7'-Dimethoxydihydrocinchroninone To a solution containing 9.2 g. of a mixture of the racemic 6',7'-dimethoxydihydrocinchonidinone and racemic 6',7'-dimethoxydihydrocinchoninone in 200 ml. of dry benzene, which was stirred under an atmosphere of dry nitrogen at 20°, was added dropwise a 25% solution of di-isobutyl aluminum hydride in toluene. After the addition of 17.5 ml., the reaction was completed. The reaction was quenched by addition of 40 ml. of methanol-water (3:2). The precipitated alumina was separated by filtration and washed thoroughly with benzene. The filtrates were combined. The benzene layer was separated, dried over anhydrous solium sulfate and evaporated to dryness. The product was separated by preparative thin layer chromatography (silica gel GF$_{254}$; chloroform-triethylaminemethanol, 85:10:5). The less polar fraction yielded 4.4 g. of amorphous, racemic 6',7'-dimethoxydihydrocinchronine.

For final purification, the base was converted to the racemic 6',7'-dimethoxydihydrocinchronine dihydrochloride, which had a melting point of 221°–225° (dec.) after recrystallization from methanol.

The more polar fractions (3.4 g.) containing racemic 6',7'-dimethoxydihydrocinchonidine gave crystals from acetone having a melting point of 155°–157°. Racemic 6',7'-dimethoxydihydrocinchonidine dihydrochloride was obtained after recrystallization from methanol and had a melting point of 208°–210° (dec.).

EXAMPLE 21

Preparation of a Mixture of racemic 6'-chlorodihydrocinchonidinone and Racemic 6'-Chlorodihydrocinchoninone from Racemic 6'-Chlorodihydrocinchotoxine To a solution containing 13.6 g. of racemic 640 -chlorodihydrocinchotoxine in 200 ml. of dichloromethane was added 16 ml. of about a 17% aqueous sodium hypochlorite and the mixture was stirred for 60 minutes. The organic phase was separated, washed with water, dried over anhydrous sodium sulfate and concentrated to a volume of about 20 ml. This solution, containing the chloramine, was added dropwise to 60 ml. of 99.5% phosphorix acid. The solvent was evaporated, and the viscous mixture was stirred at 20 ° for 17 hours. The mixture was diluted with water, and made alkaline with 6N potassium hydroxide. The alkaline aqueous phase was kept at about 70° for 30 minutes, and, thereafter, it was extracted thoroughly with ether. The ethereal phase was dried over anhydrous potassium carbonate and concentrated to dryness. The product (11.7 g.) was absorbed on 100 g. of neutral alumina, activity II. Elution with benzene and dichloromethane yielded 9.3 g. (69%) of racemic 6'-chlorodihydrocinchonidinone and racemic 6'-chlorodihydrocinchoninone which was crystallized from hexane to give 7.56 g. of a product having a melting point of 97.5°–100.5° containing some chlorine free impurity. A crystalline mixture of racemic 6'-chlorodihydrocinchoninone was prepared also by reoxidizing a mixture of racemic 6'-chlordihydrocinchonine and racemic 6'-chlorodihydrocinchonidine.

EXAMPLE 22

Preparation of Racemic 6'-Chlorodihydrocinchonidine and Racemic 6'-Chlorodihydrocinchonine from a mixture of Racemic 6'-Chlorodihydrocinchonidinone and Racemic 6'-Chlorodihydrocinchoninone To a solution of 6.73 g. of a mixture of the racemic 6'-chlorodihydrocinchonidinone and racemic 6'-chlorodihydrocinchoninone (material melting at 97.5°–100°) in 200 ml. of dry benzene, stirred under an atmosphere of dry nitrogen at 20°, was added dropwise a 25% solution of di-isobutyl alumina hydride in toluene. After addition of 13 ml., the reaction was completed. The reaction was quenched by addition of 20 ml. of methanol-water (2:3). The precipitated alumina was separated by filtration and washed thoroughly with benzene. The filtrates were combined. The benzene layer was separated and dried over anhydrous sodium sulfate and evaporated to dryness. The product (6.7 g.) could not be crystallized; therefore, it was separated by preparative thin layer chromatography (silica gel GF$_{254}$; chloroform-triethylamine = 9:1) into three fractions.

The least polar fraction (1.34 g.) was crystallized and recrystallized from acetone to give racemic 6'-chlorodihydrocinchonine having a melting point of 172.5°–173.5°. Racemic 6'-chlorodihydrocinchonine dihydrochloride has a melting point of 218°–221° (dec.).

The middle fraction (2.83 g.) was crystallized from acetone to give racemic 6'-chlorodihydrocinchonidine having a melting point of 100°–102°.

Racemic 6'-chlordihydrocinchonidine dihydrochloride had a melting point of 219°–222° (dec.) (recrystallized from methanol-ether).

EXAMPLE 23

Preparation of Racemic 6'-Methyldihydrocinchotoxine from cis (1-benzoyl-3-ethyl-4-piperidinepropionic acid ethyl ester and 6-methyl-4l -carbethoxyquinoline A solution containing 19.6 g. of cis (1-benzoyl-3-ethyl-4-piperidinepropionic acid ethyl ester in 600 ml. of dry benzene was added dropwise (3½ hours) to a reluixing mixture comprising 20.3 g. of 6-methyl-4-carbethoxyquinoline and 20.8 g. of potassium t-butoxide in 300 ml. of dry benzene under an atmosphere of dry nitrogen. The mixture was heated under reflux for an additional hour and maintained at 20° overnight. The crude mixture was extracted once with 200 ml. and three times with 20 ml. of cold 0.5N aqueous potassium hydroxide. Thereafter, the aqueous phases were washed with 4 portions of 50 ml. of benzene. The combined alkaline aqueous phases containing the crude β-ketoester were acidified with conc. HCl whereby a 6N hydrochloric acid solution was obtained, and then heated under reflux for 24 hours. The cooled mixture was made alkaline with 6N potassium hydroxide, and extracted with ether. The ethereal extracts were dried over anydrous potassium carbonate and evaporated to dryness to give 13.1 g. (68%) of racemic 6'-methyldihydrocinchotoxine.

EXAMPLE 24

Preparation of a Mixture of racemic 6'-Methyl-dihydrocinchonidinone and racemic 6'-Methyl-dihydrocinchoninone from racemic 6'-Methyl-dihydrocinchotoxine To a solution containing 13.1 g. of racemic 6'-methyl-dihydrocinchotoxine in 150 ml. of dichloromethane was added an excess of about 17% aqueous sodium hypochlorite solution, and the mixture was stirred at 20° for 1 hour. The organic phase was separated, washed with water, dried over anhydrous sodium sulfate and concentrated to 20 ml. This solution, containing the chloroamine, was added dropwise to 50 ml. of 99.5% phosphoric acid. The dichloromethane was evaporated, and the viscous mixture was stirred at 20 ° for 17 hours. Thereafter, the mixture was diluted with 20 ml. of water and made alkaline with 6N potassium hydroxide. The alkaline aqueous phase was maintained at 40° for 30 minutes, and subsequently extracted with dichloromethane. The organic extracts were dried over anhydrous sodium sulfate and concentrated to dryness to give 13.2 g. of a crystalline product. A portion was recrystallized twice from hexane to give about a 1:1 mixture of 6'-methyl-dihydrocinchonidinone and racemic 6'-methyl-dihydrocinchoninone having a melting point of 105°–108°.

EXAMPLE 25

Preparation of Racemic 6'-Methyl-dihydrocinchonidine and racemic 6'-Methyl-dihydrocinchonine from a mixture of racemic 6'-Methyl-dihydrocinchonidinone and racemic 6'-Methyl-dihydrocinchoninone 12.3 G. of a mixture comprising racemic 6'-methyldihydrocinchonidinone and racemic 6'-methyl-dihydrocinchoninone was reduced in several batches. In a typical run 4.0 g. of crystalline mixture was dissolved in 125 ml. of dry benzene, and 9 ml. of a 25% solution of di-isobutyl aluminum hydride was added dropwise at 20° to the stirred solution under an atmosphere of dry nitrogen. After about 30 minutes, the reaction was quenched by addition of 15 ml. of aqueous methanol (2:3). The precipitated alumina was separated by filtration and washed thoroughly with benzene. The filtrates were combined, and the benzene layer separated, dried over anhydrous sodium sulfate and evaporated to dryness. Trituration with acetone yielded crystalline 6'-methyldihydrocinchonidine having a melting point of 216°–218° after recrystallization from tetrahydrofuran.

Racemic 6'-methyldihydrocinchonidine dihydrochloride was crystallized from methanol-ether, m.p. 213°–216° (dec.).

The mother liquors were converted to the dihydrochloride, whereupon 2.8 g. of racemic 6'-methyldihydrocinchonine dihydrochloride was crystallized from methanol and had a melting point of 219-220° (dec.).

A portion was converted to the free base and crystallized from acetone to give racemic 6'-methyldihydrocinchonine having a melting point of 153.5°-155°.

EXAMPLE 26

Preparation of racemic 6',7'-methylenedioxy-cinchonidinone and racemic 6',7'-methylenedioxy-cinchoninone To a solution of 1.4 g. of racemic 6',7'-methylenedioxy-cinchotoxine in 80 ml. of dichloromethane was added 50 ml. of a 17% aqueous sodium hypochlorite solution. The resulting mixture was stirred at 20°-25° for 2.5 hours. The organic phase was separated and the aqueous layer was washed with dichloromethane. The combined organic solution was washed with water, dried over anhydrous sodium sulfate and concentrated to a volume of 5 ml. This solution was added dropwise to 20 ml. of 99.7% phosphoric acid with vigorous stirring. The viscous mixture was stirred at 20°-25° for 17 hours, poured onto ice and rendered alkaline by the addition of ammonium hydroxide. The mixture was kept at 55°-60° for 40 minutes and then extracted with benzene. The extract was washed with water, dried over anhydrous sodium sulfate and evaporated under reduced pressure. The crued residue (1.4 g.) was chromatographed on 14 g. of neutral alumina (Woelm), activity II, elution with 350 ml. of benzene afforded 1.17 g. (84%) of a mixture of racemic 6',7'-methylenedioxy-cinchonidinone and racemic 6',7'-methylenedioxycinchoninone.

EXAMPLE 27

Preparation of racemic 6',7'-methylenedioxy-dihydrocinchonidine and racemic 6',7'-methylenedioxy-dihydrocinchonine A solution of 4.9 g. of racemic N-benzoyl-6',7'-methylenedioxy-dihydrocinchotoxine in 200 ml. of 6N hydrochloric acid was kept at reflux temperature for 15 hours. The cooled reaction mixture was rendered alkaline by addition of 6N sodium hydroxide and extracted with three 200 ml.-portions of dichloromethane. The combined organic extract was washed with water, dried over sodium sulfate and evaporated under reduced pressure to give 3.61 g. of solid racemic 6',7'-methylenedioxy-dihydrocinchotoxine.

A solution of the crude compound in 250 ml. of dichloromethane was added to 200 ml. of a 17% aqueous sodium hypochlorite solution. The resulting mixture was stirred at 20°-25° for 2.5 hours. The organic phase was separated and the aqueous layer was washed with dichloromethane. The combined organic solution was washed with water, dried over anhydrous sodium sulfate and concentrated to a volume of 15 ml. This solution was added dropwise to 60 ml of 99.7% phosphoric acid with vigorous stirring. The viscous mixture was stirred at 20°-25° for 17 hours, poured onto 300 g. of ice and rendered alkaline by the addition of ammonium hydroxide. The mixture was kept at 55-60° for 40 minutes and extracted with three 100 ml.-portions of benzene. The combined extract was washed with water, dried over anhydrous sodium sulfate and evaporated under reduced pressure to afford 2.58 g. of a crude mixture of racemic 6',7'-methylenedioxy-dihydrocinchonidinone and racemic 6',7'-methylenedioxy-dihydrocinchoninone.

To a solution of 2.58 g. of the crude mixture of racemic 6',7'-methylenedioxydihydrocinchonidinone and racemic 6',7'-methylenedioxy-dihydrocinchoninone in 50 ml of anhydrous benzene was added dropwise with ice cooling 10 ml. of a 25% solution of di-isobutyl aluminum hydride in toluene under an atmosphere of dry nitrogen. The reaction was quenched after 1 hour by adding 10 ml. of water-methanol (1:1) with vigorous stirring. The precipitate was collected by filtration and washed thoroughly with methanol. The filtrate was dried over anhydrous sodium sulfate and evaporated to dryness. A solution of the residue in chloroform was washed successively with 1N sodium hydroxide and water, dried over anhydrous sodium sulfate, and evaporated to dryness. The crude product (2.64 g. of yellow solid material) was chromatographed on Merck F-254 silica gel preparative plates (20×20×0.2 cm. ) with chloroform-triethylamine (85:10) as the solvent mixture. The plates were developed six times. Elution of the lower of two major bands with methanol-chloroform and crystallization of the eluate from acetone gave racemic 6',7'-methylenedioxy-dihydrocinchonidine, m.p. 232-233° with dec. >226°.

Elution of the outer major band with methanol-chloroform and crystallization of the eluate from acetone afforded 6',7'-methylenedioxy-dihydrocinchonine, m.p. 234°–235°.

EXAMPLE 28

Preparation of Racemic 7'-trifluoromethyl-dihydrocinchonidine and 7'-trifluoromethyl-dihydrocinchonine from the mixture of racemic 7'-trifluoromethyl-dihydrocinchonidinone and 7'-trifluoromethyl-dihydrocinchoninone To the solution of 0.229 g. of a mixture of racemic 7'-trifluoromethyl-dihydrocinchonidinone and 7'-trifluoromethyl-dihydrocinchoninone in 20 ml. of anhydrous benzene under a nitrogen atmosphere was added 0.5 ml. of 25% diisobutyl-aluminum hydride in hexane. The reaction mixture was then stirred at room temperature until the absence of starting ketone was observed on thin layer chromatography. The excess of hydride was decomposed with water. Thereafter, the pH was adjusted to 10 with 1N sodium hydroxide, and the mixture was extracted thoroughly with chloroform. The chloroform extract was dried over sodium sulfate anhydrous and evaporated to dryness. The crude product was chromatographed on four preparative silica gel paltes with 89:10:1 chloroform-triethylamine-methanol solvent system to give 45 mg. of racemic 7′-trifluoromethyl-dihydrocinchonine, m.p. 215°–218° (from acetone) and 139 mg. of racemic 7′-trifluoromethyl-dihydrocinchonidine, m.p. 169°–171° (from acetone).

| Tablet Formulation | |
|---|---|
| | Per Tablet |
| Racemic 7′-methoxy-dihydrocinchonidinone | 25.00 mg. |
| Dicalcium Phosphate Dihydrate, Unmilled | 175.00 mg. |
| Corn Starch | 24.00 mg. |
| Magnesium Stearate | 1.00 mg. |
| Total Weight | 225.00 mg. |

Procedure:

25 Parts of racemic 7′-methoxy-dihydrocinchonidinone and 24 parts of corn starch were mixed together and passed through a No. 00 screen in Model "J" Fitzmill with hammers forward. This premix was then mixed with 175 parts of dicalcium phosphate and one-half part of magnesium stearate, passed through a No. 1A screen in Model "J" Fitzmill with knives forward, and slugged. The slugs were passes through a No. 2A plate in a Model "D" Fitzmill at slow speed with knives forward, and the remaining magnesium stearate was added. The mixture was mixed and compressed.

EXAMPLE 30

| Capsule Formulation | |
|---|---|
| | Per Capsule |
| Racemic 7′-methoxy-dihydrocinchonidinone | 50 mg. |
| Corn Starch, U.S.P. | 150 mg. |
| Talc, U.S.P. | 10 mg. |
| Total Weight | 210 mg. |

Procedure:

Fifty parts of racemic 7′-methoxy-dihydrocinchonidinone were mixed with 150 parts of corn starch in a suitable mixer. The mixture was further blended by passing through a Fitzpatrick Comminuting Machine with a No. 1A screen with knives forward. The blended powder was returned to the mixer and 10 parts of talc were added and blended thoroughly. The mixture was filled into No. 4 hard shell gelatin capsules on a Parke Davis capsulating machine.

EXAMPLE 31

| Suppository Formulation | |
|---|---|
| | Per 1.3 Gm. Suppository |
| Racemic dihydroquininone | 0.025 gm. |
| Hydrogenated Coconut Oil | 1.230 gm. |
| Carnauba Wax | 0.045 gm. |

Procedure:

123 Parts of hydrogenated coconut oil (Wecobee M - E. F. Drew Co., New York, New York) and 4.5 parts of carnauba wax were melted in a suitable size glass lined container (stainless steel may also be used), mixed well and cooled to 45° C. 2.5 Parts of racemic dihydroquininone, which had been reduced to a fine powder with no lumps, was added and stirred until completely and uniformly dispersed. The mixture was poured into suppository molds to yield suppositories having an individual weight of 1.3 gms. The suppositories were cooled and removed from molds and individually wrapped in wax paper for packaging.

We claim:
1. Racemic 6′-chloro-dihydrocinchoninone.
2. An antipode of 7′-chlorodihydrocinchoninone.
3. Racemic 6′-chloro-dihydrocinchonidinone.
4. An antipode of 7′-chlorodihydorcinchonidinone.

* * * * *

UNITED STATES PATENT AND TRADEMARK OFFICE
CERTIFICATE OF CORRECTION

PATENT NO. : 4,096,146
DATED : June 20, 1978
INVENTOR(S) : Gutzwiller et al

It is certified that error appears in the above-identified patent and that said Letters Patent are hereby corrected as shown below:

Column 42, claim 4, line 37, "7'-chlorodihydorcinchonidinone" should be:

7'-chlorodihydrocinchonidinone

Signed and Sealed this

Third Day of April 1979

[SEAL]

Attest:

RUTH C. MASON
Attesting Officer

DONALD W. BANNER
Commissioner of Patents and Trademarks